US010213334B2

(12) United States Patent
Nofzinger et al.

(10) Patent No.: US 10,213,334 B2
(45) Date of Patent: *Feb. 26, 2019

(54) APPARATUS AND METHOD FOR MODULATING SLEEP

(71) Applicants: Ebb Therapeutics, Inc., Pittsburgh, PA (US); University of Pittsburgh—Of the Commonwealth System of Higher Education, Pittsburgh, PA (US)

(72) Inventors: Eric A. Nofzinger, Allison Park, PA (US); Jeffrey J. Schirm, Monroeville, PA (US); Damian F. Rippole, Coraopolis, PA (US); Craig B. Reynolds, Kennesaw, GA (US); Robert E. Tucker, Sanibel, FL (US)

(73) Assignees: Ebb Therapeutics, Inc., Pittsburgh, PA (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 408 days.

This patent is subject to a terminal disclaimer.

(21) Appl. No.: 14/938,705

(22) Filed: Nov. 11, 2015

(65) Prior Publication Data

US 2016/0128864 A1    May 12, 2016

Related U.S. Application Data

(63) Continuation of application No. 14/341,642, filed on Jul. 25, 2014, now Pat. No. 9,211,212, which is a
(Continued)

(51) Int. Cl.
*A61F 7/00* (2006.01)
*A61F 7/02* (2006.01)
(Continued)

(52) U.S. Cl.
CPC .............. *A61F 7/007* (2013.01); *A61F 7/02* (2013.01); *A61M 21/02* (2013.01);
(Continued)

(58) Field of Classification Search
None
See application file for complete search history.

(56) References Cited

U.S. PATENT DOCUMENTS

| 222,690 A | 12/1879 | Goldschmidt |
| 301,931 A | 7/1884 | Smith et al. |

(Continued)

FOREIGN PATENT DOCUMENTS

| EP | 1977710 | 10/2008 |
| EP | 2359781 | 8/2011 |

(Continued)

OTHER PUBLICATIONS

Mallick et al; Basal forebrain thermoregulatory mechanism modulates auto-regulated sleep; Frontiers in Neurology; 10.3389/fneur.2012.00102 (8 pages); Jun. 27, 2012.
(Continued)

*Primary Examiner* — Kaitlyn Smith
(74) *Attorney, Agent, or Firm* — Shay Glenn LLP

(57) ABSTRACT

Apparatuses and methods to enhance sleep, reduce sleep onset latency, extend sleep duration and/or increasing the duration of deeper sleep stages relative to stage 1 sleep. In general, these apparatuses and methods apply and maintain one or more target "warm" temperatures to a subject's forehead for a time period. The target temperature may be between 25° C. and 42° C. The target temperature may be a fixed amount greater than ambient temperature. The time period may be a fixed time period or a variable time period. These methods and apparatuses may limit the application of thermal energy to the subject's forehead region.

26 Claims, 22 Drawing Sheets

Related U.S. Application Data continuation-in-part of application No. 12/288,417, filed on Oct. 20, 2008, now Pat. No. 9,492,313, which is a continuation-in-part of application No. 11/788,694, filed on Apr. 20, 2007, now Pat. No. 8,236,038.

(60) Provisional application No. 60/793,680, filed on Apr. 20, 2006, provisional application No. 61/859,161, filed on Jul. 26, 2013.

(51) Int. Cl.
    A61F 7/10        (2006.01)
    A61M 21/02       (2006.01)
    A61M 21/00       (2006.01)
    A61B 17/00       (2006.01)

(52) U.S. Cl.
    CPC ........... A61B 2017/00132 (2013.01); A61F 2007/0002 (2013.01); A61F 2007/0007 (2013.01); A61F 2007/0054 (2013.01); A61F 2007/0056 (2013.01); A61F 2007/0071 (2013.01); A61F 2007/0075 (2013.01); A61F 2007/0076 (2013.01); A61F 2007/0095 (2013.01); A61M 2021/0066 (2013.01)

(56) References Cited

U.S. PATENT DOCUMENTS

| | | |
|---|---|---|
| 683,991 A | 10/1901 | Rowe |
| 737,473 A | 8/1903 | Porter |
| 805,371 A | 11/1905 | Meinecke et al. |
| 919,614 A | 4/1909 | Meinecke |
| 1,002,021 A | 8/1911 | Barnes |
| 1,127,221 A | 2/1915 | Finkelstein |
| 1,318,411 A | 10/1919 | Rozene |
| 1,322,984 A | 11/1919 | Wesley |
| 1,345,906 A | 7/1920 | Augustine |
| 1,511,775 A | 10/1924 | Frederic et al. |
| 1,522,295 A | 1/1925 | Gee |
| 1,567,931 A | 12/1925 | Epler |
| 1,743,244 A | 1/1930 | Shulman |
| 1,769,186 A | 7/1930 | Morris |
| 1,870,143 A | 8/1932 | Roux |
| 1,964,655 A | 6/1934 | Williamson |
| 2,049,723 A | 8/1936 | Pomeranz |
| 2,158,571 A | 5/1939 | Culp |
| 2,320,467 A | 6/1943 | Rabil |
| 2,726,658 A | 12/1955 | Chessey |
| 3,244,210 A | 4/1966 | Giacomo |
| 3,463,161 A | 8/1969 | Andrassy |
| 3,587,577 A | 6/1971 | Smirnov et al. |
| 3,696,814 A | 10/1972 | Umemoto |
| 3,717,145 A | 2/1973 | Berndt et al. |
| 3,895,638 A | 7/1975 | Ito |
| 3,908,655 A | 9/1975 | Lund |
| 3,979,345 A | 9/1976 | Yates et al. |
| 3,988,568 A | 10/1976 | Mantell |
| 4,118,946 A | 10/1978 | Tubin |
| 4,172,495 A | 10/1979 | Zebuhr et al. |
| 4,204,543 A | 5/1980 | Henderson |
| 4,356,709 A | 11/1982 | Alexander |
| 4,425,916 A | 1/1984 | Bowen |
| 4,466,439 A | 8/1984 | Moore |
| 4,483,021 A | 11/1984 | McCall |
| 4,566,455 A | 1/1986 | Kramer |
| 4,574,411 A | 3/1986 | Yagi |
| 4,691,762 A | 9/1987 | Elkins et al. |
| 4,742,827 A | 5/1988 | Lipton |
| 4,753,242 A | 6/1988 | Saggers |
| 4,765,338 A | 8/1988 | Turner et al. |
| 4,781,193 A | 11/1988 | Pagden |
| 4,854,319 A | 8/1989 | Tobin |
| 4,891,501 A | 1/1990 | Lipton |
| 4,920,963 A | 5/1990 | Brader |
| 4,961,422 A | 10/1990 | Marchosky et al. |
| 5,097,828 A | 3/1992 | Deutsch |
| 5,097,829 A | 3/1992 | Quisenberry |
| 5,163,425 A | 11/1992 | Nambu et al. |
| 5,183,058 A | 2/1993 | Janese |
| 5,184,613 A | 2/1993 | Mintz |
| 5,197,466 A | 3/1993 | Marchosky et al. |
| 5,228,431 A | 7/1993 | Giarretto |
| 5,261,399 A | 11/1993 | Klatz et al. |
| 5,274,865 A | 1/1994 | Takehashi |
| 5,292,347 A | 3/1994 | Pompei |
| 5,305,470 A | 4/1994 | Mckay |
| 5,305,471 A | 4/1994 | Steele et al. |
| 5,314,456 A | 5/1994 | Cohen |
| 5,327,585 A | 7/1994 | Karlan |
| 5,342,411 A | 8/1994 | Maxted et al. |
| 5,344,437 A | 9/1994 | Pistay |
| 5,356,426 A | 10/1994 | Delk et al. |
| 5,400,617 A | 3/1995 | Ragonesi et al. |
| 5,409,500 A | 4/1995 | Dyrek |
| 5,441,476 A | 8/1995 | Kitado et al. |
| 5,469,579 A | 11/1995 | Tremblay et al. |
| 5,531,777 A | 7/1996 | Goldstein et al. |
| 5,545,199 A | 8/1996 | Hudson |
| 5,603,728 A | 2/1997 | Pachys |
| 5,609,619 A | 3/1997 | Pompei |
| 5,643,336 A | 7/1997 | Lopez-Claros |
| 5,658,324 A | 8/1997 | Bailey, Sr. et al. |
| 5,715,533 A | 2/1998 | Stein |
| 5,755,756 A | 5/1998 | Freedman, Jr. et al. |
| 5,837,002 A | 11/1998 | Augustine et al. |
| 5,848,981 A | 12/1998 | Herbranson |
| 5,867,999 A | 2/1999 | Bratton et al. |
| 5,871,526 A | 2/1999 | Gibbs et al. |
| 5,895,418 A | 4/1999 | Saringer |
| 5,897,581 A | 4/1999 | Fronda et al. |
| 5,897,582 A | 4/1999 | Agnatovech et al. |
| 5,916,242 A | 6/1999 | Schwartz |
| 5,948,012 A | 9/1999 | Mahaffey et al. |
| 5,950,234 A | 9/1999 | Leong et al. |
| 5,957,963 A | 9/1999 | Dobak, III |
| 5,957,964 A | 9/1999 | Ceravolo |
| 6,010,528 A | 1/2000 | Augustine et al. |
| 6,017,337 A | 1/2000 | Pira |
| 6,030,412 A | 2/2000 | Klatz et al. |
| 6,051,019 A | 4/2000 | Dobak |
| 6,083,254 A | 7/2000 | Evans |
| 6,113,626 A | 9/2000 | Clifton et al. |
| 6,126,680 A | 10/2000 | Wass |
| 6,156,057 A | 12/2000 | Fox |
| 6,156,059 A | 12/2000 | Olofsson |
| 6,183,501 B1 | 2/2001 | Latham |
| 6,197,045 B1 | 3/2001 | Carson |
| 6,228,376 B1 | 5/2001 | Misumi et al. |
| 6,231,595 B1 | 5/2001 | Dobak, III |
| 6,248,126 B1 | 6/2001 | Lesser |
| 6,277,143 B1 | 8/2001 | Klatz et al. |
| 6,295,819 B1 | 10/2001 | Mathiprakasam et al. |
| 6,312,453 B1 | 11/2001 | Stefanile et al. |
| 6,363,285 B1 | 3/2002 | Wey |
| 6,375,673 B1 | 4/2002 | Clifton et al. |
| 6,375,674 B1 | 4/2002 | Carson |
| 6,409,746 B1 | 6/2002 | Igaki et al. |
| 6,416,532 B1 | 7/2002 | Fallik |
| 6,461,379 B1 | 10/2002 | Carson et al. |
| 6,500,201 B1 | 12/2002 | Tsuchiya et al. |
| 6,511,502 B2 | 1/2003 | Fletcher |
| 6,516,624 B1 | 2/2003 | Ichigaya |
| 6,523,354 B1 | 2/2003 | Tolbert |
| 6,551,347 B1 | 4/2003 | Elkins |
| 6,554,787 B1 | 4/2003 | Griffin et al. |
| 6,581,400 B2 | 6/2003 | Augustine et al. |
| 6,599,312 B2 | 7/2003 | Dobak, III |
| 6,610,084 B1 | 8/2003 | Torres |
| 6,629,990 B2 | 10/2003 | Putz et al. |
| 6,669,715 B2 | 12/2003 | Hoglund et al. |
| 6,673,098 B1 | 1/2004 | Machold et al. |
| 6,682,552 B2 | 1/2004 | Ramsden et al. |
| 6,692,518 B2 | 2/2004 | Carson |

(56) References Cited

U.S. PATENT DOCUMENTS

| | | |
|---|---|---|
| 6,699,267 B2 | 3/2004 | Voorhees et al. |
| 6,736,837 B2 | 5/2004 | Fox |
| 6,740,109 B2 | 5/2004 | Dobak, III |
| 6,740,110 B2 | 5/2004 | Babcock |
| 6,770,085 B1 | 8/2004 | Munson |
| 6,845,520 B2 | 1/2005 | Kim |
| 6,854,128 B1 | 2/2005 | Faulk |
| 6,881,219 B1 | 4/2005 | Agarwal et al. |
| 6,921,374 B2 | 7/2005 | Augustine |
| 6,929,656 B1 | 8/2005 | Lennox |
| 6,962,600 B2 | 11/2005 | Lennox et al. |
| 6,979,345 B2 | 12/2005 | Werneth |
| 7,008,445 B2 | 3/2006 | Lennox |
| 7,044,960 B2 | 5/2006 | Voorhees et al. |
| 7,052,509 B2 | 5/2006 | Lennox et al. |
| 7,056,334 B2 | 6/2006 | Lennox |
| 7,077,858 B2 | 7/2006 | Fletcher et al. |
| 7,087,075 B2 | 8/2006 | Briscoe et al. |
| 7,146,211 B2 | 12/2006 | Frei et al. |
| 7,152,412 B2 | 12/2006 | Harvie |
| 7,179,280 B2 | 2/2007 | Mills |
| 7,182,777 B2 | 2/2007 | Mills |
| 7,189,252 B2 | 3/2007 | Krueger |
| 7,229,468 B2 | 6/2007 | Wong, Jr. et al. |
| 7,309,348 B2 | 12/2007 | Streeter et al. |
| 7,559,907 B2 | 7/2009 | Krempel et al. |
| 7,637,931 B2 | 12/2009 | Heaton |
| 7,744,640 B1 | 6/2010 | Faries, Jr. et al. |
| 7,854,754 B2 | 12/2010 | Ting et al. |
| 7,875,066 B2 | 1/2011 | Cohen et al. |
| 7,877,827 B2 | 2/2011 | Marquette et al. |
| 7,909,861 B2 | 3/2011 | Balachandran et al. |
| 7,930,772 B2 | 4/2011 | Fontanez |
| 8,052,624 B2 | 11/2011 | Buchanan et al. |
| 8,236,038 B2 | 8/2012 | Nofzinger |
| 8,425,583 B2 | 4/2013 | Nofzinger |
| 8,784,293 B2 | 7/2014 | Berka et al. |
| 9,089,400 B2 | 7/2015 | Nofzinger |
| 9,211,212 B2 | 12/2015 | Nofzinger et al. |
| 2001/0000029 A1 | 3/2001 | Misumi et al. |
| 2001/0025191 A1 | 9/2001 | Montgomery |
| 2001/0039442 A1 | 11/2001 | Gorge et al. |
| 2001/0045104 A1 | 11/2001 | Bailey, Sr. et al. |
| 2002/0026226 A1 | 2/2002 | Ein |
| 2002/0095198 A1 | 7/2002 | Whitebook et al. |
| 2002/0103520 A1 | 8/2002 | Latham |
| 2002/0156509 A1 | 10/2002 | Cheung |
| 2003/0109911 A1 | 6/2003 | Lachenbruch et al. |
| 2003/0130651 A1 | 7/2003 | Lennox |
| 2003/0149461 A1 | 8/2003 | Johnson |
| 2003/0171685 A1 | 9/2003 | Lesser et al. |
| 2003/0195439 A1 | 10/2003 | Caselnova |
| 2004/0010178 A1 | 1/2004 | Buckner |
| 2004/0024432 A1 | 2/2004 | Castilla |
| 2004/0049134 A1 | 3/2004 | Tosaya et al. |
| 2004/0059400 A1 | 3/2004 | Lin |
| 2004/0064170 A1 | 4/2004 | Radons et al. |
| 2004/0073280 A1 | 4/2004 | Dae et al. |
| 2004/0073281 A1 | 4/2004 | Caselnova |
| 2004/0159109 A1 | 8/2004 | Harvie |
| 2004/0171970 A1 | 9/2004 | Schleuniger et al. |
| 2004/0186541 A1 | 9/2004 | Agarwal et al. |
| 2004/0249427 A1 | 12/2004 | Nabilsi |
| 2005/0065584 A1 | 3/2005 | Schiff et al. |
| 2005/0087194 A1 | 4/2005 | Scott |
| 2005/0107851 A1 | 5/2005 | Taboada et al. |
| 2005/0131504 A1 | 6/2005 | Kim |
| 2005/0143797 A1 | 6/2005 | Parish et al. |
| 2006/0024358 A1 | 2/2006 | Santini et al. |
| 2006/0122673 A1 | 6/2006 | Callister et al. |
| 2006/0149119 A1 | 7/2006 | Wang |
| 2006/0161230 A1 | 7/2006 | Craven |
| 2006/0173396 A1 | 8/2006 | Hatamian et al. |
| 2006/0198874 A1 | 9/2006 | Stanley |
| 2006/0235495 A1 | 10/2006 | Tsai |
| 2006/0235498 A1 | 10/2006 | Mollendorf et al. |
| 2006/0251743 A1 | 11/2006 | Karita |
| 2006/0293732 A1 | 12/2006 | Collins et al. |
| 2007/0010861 A1 | 1/2007 | Anderson et al. |
| 2007/0055330 A1 | 3/2007 | Rutherford |
| 2007/0123758 A1 | 5/2007 | Miesel et al. |
| 2007/0207220 A1 | 9/2007 | Luedtke et al. |
| 2007/0282249 A1 | 12/2007 | Quisenberry et al. |
| 2007/0282406 A1 | 12/2007 | Dow |
| 2008/0015665 A1 | 1/2008 | Lachenbruch |
| 2008/0033518 A1 | 2/2008 | Rousso et al. |
| 2008/0046026 A1 | 2/2008 | Pless et al. |
| 2008/0046047 A1 | 2/2008 | Jacobs |
| 2008/0097560 A1 | 4/2008 | Radziunas et al. |
| 2008/0097561 A1 | 4/2008 | Melsky et al. |
| 2008/0103568 A1 | 5/2008 | Dow |
| 2008/0140096 A1 | 6/2008 | Svadovskiy |
| 2008/0168605 A1 | 7/2008 | Wolske |
| 2008/0188915 A1 | 8/2008 | Mills et al. |
| 2008/0228248 A1 | 9/2008 | Guyuron et al. |
| 2008/0249439 A1 | 10/2008 | Tracey et al. |
| 2008/0249520 A1 | 10/2008 | Dunning et al. |
| 2008/0269852 A1 | 10/2008 | Lennox et al. |
| 2008/0288033 A1 | 11/2008 | Mason et al. |
| 2008/0300529 A1 | 12/2008 | Reinstein |
| 2009/0024043 A1 | 1/2009 | MacLeod et al. |
| 2009/0049694 A1 | 2/2009 | Morris |
| 2009/0054958 A1 | 2/2009 | Nofzinger |
| 2009/0198311 A1 | 8/2009 | Johnson et al. |
| 2009/0236893 A1 | 9/2009 | Ehlers et al. |
| 2009/0306748 A1 | 12/2009 | Mollendorf et al. |
| 2009/0312676 A1 | 12/2009 | Rousso et al. |
| 2009/0312823 A1 | 12/2009 | Patience et al. |
| 2010/0030306 A1 | 2/2010 | Edelman et al. |
| 2010/0087701 A1 | 4/2010 | Berka et al. |
| 2010/0122398 A1 | 5/2010 | Luciano |
| 2010/0198281 A1 | 8/2010 | Chang et al. |
| 2010/0198318 A1 | 8/2010 | Rogers |
| 2010/0211142 A1 | 8/2010 | Rogers et al. |
| 2010/0241200 A1 | 9/2010 | Bruder et al. |
| 2010/0312317 A1 | 12/2010 | Baltazar |
| 2010/0331752 A1 | 12/2010 | Cumming et al. |
| 2011/0125233 A1 | 5/2011 | Shen et al. |
| 2011/0184502 A1 | 7/2011 | Bruder |
| 2011/0218421 A1 | 9/2011 | Hempel et al. |
| 2011/0282269 A1 | 11/2011 | Quisenberry et al. |
| 2012/0150268 A1 | 6/2012 | Doherty et al. |
| 2012/0302942 A1 | 11/2012 | DiPierro et al. |
| 2012/0310312 A1 | 12/2012 | Yee |
| 2013/0007945 A1 | 1/2013 | Krondahl |
| 2013/0103125 A1 | 4/2013 | Radspieler et al. |
| 2013/0131464 A1 | 5/2013 | Westbrook et al. |
| 2013/0202668 A1 | 8/2013 | Prost et al. |
| 2013/0289680 A1 | 10/2013 | Hasegawa |
| 2014/0303698 A1 | 10/2014 | Benyaminpour et al. |
| 2014/0343069 A1 | 11/2014 | Laiji et al. |
| 2015/0238725 A1 | 8/2015 | Tucker et al. |
| 2015/0290420 A1 | 10/2015 | Nofzinger |
| 2015/0352314 A1 | 12/2015 | Walker et al. |

FOREIGN PATENT DOCUMENTS

| | | |
|---|---|---|
| GB | 460200 A | 1/1937 |
| GB | 461294 A | 2/1937 |
| JP | 2-20522 | 2/1990 |
| JP | 10-192331 | 7/1998 |
| JP | 11-042282 | 2/1999 |
| JP | 2003164496 | 6/2003 |
| JP | 2004189999 A | 7/2004 |
| JP | 3730096 B | 10/2005 |
| JP | 2005274013 | 10/2005 |
| JP | 2006102020 | 4/2006 |
| JP | 20007175476 A | 7/2007 |
| WO | WO90/01911 A1 | 3/1990 |
| WO | WO92/20309 A1 | 11/1992 |
| WO | WO94/00086 A1 | 1/1994 |
| WO | WO95/10251 A1 | 4/1995 |
| WO | WO96/10379 A2 | 4/1996 |
| WO | WO96/31136 A1 | 10/1996 |

(56) References Cited

FOREIGN PATENT DOCUMENTS

| WO | WO97/36560 A1 | 10/1997 |
| WO | WO98/56310 A1 | 12/1998 |
| WO | WO99/08632 A1 | 2/1999 |
| WO | WO00/03666 A1 | 1/2000 |
| WO | WO00/09052 A1 | 2/2000 |
| WO | WO01/39704 A1 | 6/2001 |
| WO | WO02/05736 A2 | 1/2002 |
| WO | WO02/34177 A1 | 5/2002 |
| WO | WO03/092539 A2 | 11/2003 |
| WO | WO2004/065862 A2 | 8/2004 |
| WO | WO2004/111741 A1 | 12/2004 |
| WO | WO2005/007060 A2 | 1/2005 |
| WO | WO2005/076806 A2 | 8/2005 |
| WO | WO2005/120428 A1 | 12/2005 |
| WO | WO2006/073915 A2 | 7/2006 |
| WO | WO2006/086086 A2 | 8/2006 |
| WO | WO2007/005026 A1 | 1/2007 |
| WO | WO2007/101039 A1 | 9/2007 |
| WO | WO2008/099017 A1 | 8/2008 |
| WO | WO2008/129357 A2 | 10/2008 |
| WO | WO2008/142650 A1 | 11/2008 |
| WO | WO2008/151260 A2 | 12/2008 |
| WO | WO2009/073208 A1 | 6/2009 |
| WO | WO2009/122336 A1 | 10/2009 |
| WO | WO2009/147413 A1 | 12/2009 |
| WO | WO2011/161571 A1 | 12/2011 |
| WO | WO2012/012683 A1 | 1/2012 |
| WO | WO2012/028730 A1 | 3/2012 |
| WO | WO2012/083151 A1 | 6/2012 |
| WO | WO2015/071810 A1 | 5/2015 |
| WO | WO2015/148411 A1 | 10/2015 |

OTHER PUBLICATIONS

Nofzinger et al.; U.S. Appl. No. 15/521,375 entitled "Method and apparatuses for modulating sleep by chemical activation of temperature receptors," filed Apr. 24, 2017.

Nofzinger et al.; U.S. Appl. No. 15/597,057 entitled "Forehead cooling method and device to stimulate the parasympathetic nervous system for the treatment of insomnia," filed May 16, 2017.

Tucker; U.S. Appl. No. 15/597,078 entitled "Tetherless wearable thermal devices and methods of using them for treatment of sleeping and neurological disorders," filed May 16, 2017.

Adam et al.; Physiological and psychological differences between good and poor sleepers; J. psychiat. Res.; 20(4); pp. 301-316; 1986 (year of pub. sufficiently earlier than effective US filing date any foreign priority date).

Ahiska et al.; Control of a thermoelectric brain cooler by adaptive neuro-fuzzy interference system; Instrumentation Science and Technology; vol. 36(6); pp. 636-655; Oct. 2008.

Ahmed et al.; Development of a cooling unit for the emergency treatment of head injury; World Congress on Medical Physics and Biomedical Engineering 2006; IFMBE Proceedings; vol. 14(5); Track 19; pp. 3243-3246; Aug. 2006 (copyright 2007).

Alam et al.; Local preoptic / anterior hypothalamic warming alters spontaneous and evoked neuronal activity in the magno-cellular basal forebrain; Brian Research; 696; pp. 221-230; Oct. 1995.

Alam et al.; Preoptic / anterior hypothalamic neurons: thermosensitivity in rapid eye movement sleep; Am. J. Physiol.Regul. Integr. Comp. Physiol.; 269; pp. R1250-R1257; Nov. 1995.

Alfoldi et al.; Brian and core temperatures and peripheral vasomotion during sleep and wakefulness at various ambient temperatures in the rat; Pflugers Arch.; 417; pp. 336-341; Nov. 1990.

Aschoff, Circadian Rhythms in Man, Science, vol. 148, pp. 1427-1432, Jun. 11, 1965.

Baker et al.; Persistence of sleep-temperature coupling after suprachiasmatic nuclei lesions in rats; Am. J. Physiol. Regul. Integr. Comp. Physiol.; 289(3); pp. R827-R838; Sep. 2005.

Boulant et al.; Hypothalamic neuronal responses to peripheral and deep-body temperatures; Am. J. of Physiol.; 225(6); pp. 1371-1374; Dec. 1973.

Boulant et al.; Temperature receptors in the central nervous system; Ann. Rev. Physiol.; 48; pp. 639-654; 1986 (year of pub. sufficiently earlier than effective US filing date and any foreign priority date).

Boulant et al.; The effects of spinal and skin temperatures on the firing rate and thermosensitivity of preoptic neurones; J. Physiol.; 240(3); pp. 639-660; Aug. 1974.

Boulant; Hypothalamic mechanisms in thermoregulation; Fed. Proc.; 40(14); pp. 2843-2850; Dec. 1981.

Brown; Toe temperature change: a measure of sleep onset?; Walking and Sleeping; 3(4); pp. 353-359; Sep.-Dec. 1979.

Clarkson et al.; Thermal neutral temperature of rats in helium-oxygen, argon-oxygen, and air; Am. J. Physiol.; 222(6); pp. 1494-1498; Jun. 1972.

Crawshaw et al.; Effect of local cooling on sweating rate and cold sensation; Pfugers Arch.; 354(1); pp. 19-27; 1975 (year of pub. sufficiently earlier than effective US filing date and any foreign priority date).

Diao et al., Cooling and Rewarming for Brain Ischemia or Injury: Theoretical Analysis, Annals of Biomedical Engineering, vol. 31, p. 346-353, Mar. 2003.

Gong et al.; Sleep-related c-Fos protien expression in the preoptic hypothalamus: effects of ambient warming; Am. J. Physiol. Regul. Integr. Comp. Physiol.; 279(6); pp. R2079-R2088; Dec. 2000.

Gordon; Relationship between preferred ambient temperature and autonomic thermoregulatory function in rat; Am. J. Physiol. Regul. Integr. Comp. Physiol.; 252; pp. R1130-R1137; 1987 (year of pub. sufficiently earlier than effective US filing date and any foreign priority date).

Gulia et al.; Ambient temperature related sleep changes in rats neonatally treated with capsaicin; Physiol. Behav.; 85(4); pp. 414-418; Jul. 21, 2005.

Guzman-Marin et al.; Discharge modulation of rat dorsal raphe neurons during sleep and waking: effects of preoptic / basal forebrain warming; Brain Res.; 875(1-2); pp. 23-34; Sep. 1, 2000.

Hajos et al.; The capsaicin sensitivity of the preoptic region is preserved in adult rats pretreated as neonates, but lost in rats pretreated as adults; Naunyn-Schmiedeberg's Arch. Pharmacol.; 324(3); pp. 219-222; Nov. 1983.

Haskell et al.; The effects of high and low ambient temperatures on human sleep stages; Electroencephalogr. Clin. Neurophysiol.; 51(5); pp. 494-501; May 1981.

Hayashi et al., The alerting effects of caffeine, bright light and face washing after a short daytime nap, Clinical Neurophysiology, 114(12), pp. 2268-2278, Dec. 2003.

Hensley et al.; 50 years of computer simulation of the human thermoregulatory system; J. Biomech. Eng.; 135(2); pp. 021005-1-021005-9; Feb. 2013.

Herrington; The heat regulation of small laboratory animals at various environmental temperatures; Am. J. of Physiol.; 129; pp. 123-139; Mar. 31, 1940.

Heuvel et al.; Changes in sleepiness and body temperature precede nocturnal sleep onset: evidence from a polsomnographic study in young men; J. Sleep Res.; 7(3); pp. 159-166; Sep. 1998.

Horne et al., Vehicle accidents related to sleep: a review, Occup Environ Med, vol. 56(5), pp. 289-294 (full text version 13 pgs.), May 1999.

Horne et al.; Exercise and sleep: body-heating effects; Sleep; 6(1); pp. 36-46; 1983 (year of pub. sufficiently earlier than effective US filing date and any foreign priority date).

Horne et al.; Slow wave sleep elevations after body heating: proximity to sleep and effects of aspirin; Sleep; 10(4); pp. 383-392; Aug. 1987.

Iber et al.; The AASM manual for the scoring of sleep and associatted events. The rules, terminology and technical specifications; Westchester, IL; © 2007; 57 pages; Oct. 28, 2014; retrieved from the internet (http://www.nswo.nl/userfiles/files/AASM%20-%20Manual%20for%20the%20Scoring%20ofSleep%20and%20Associted%20Events%20-%2005-2007_2.pdf).

Iwata et al., Brain temperature in newborn piglets under selective head cooling with minimal systemic hypothermia, Pediatrics International, 45(2), pp. 163-168; Apr. 2003.

(56) References Cited

OTHER PUBLICATIONS

John et al.; Changes in sleep-wakefulness after kainic acid lesion of the preoptic area in rats; Jpn J. Physiol.; 44; pp. 231-242; 1994 (year of pub. sufficiently earlier than effective US filing date and any foreign priority date).

John et al.; Effect of NMDA lesion of the medial preoptic neurons on sleep and other functions; Sleep; 21(6); pp. 587-598; Sep. 15, 1998.

Khubchandani et al.; Functional MRI shows activation of the medial preoptic area during sleep; NeuroImage; 26; pp. 29-35; May 15, 2005.

Krauchi et al., Circadian rhythm of heat production, heart rate, and skin and core temperature under unmasking conditions in men, American Physiological Society, 267 (3 Pt 2), pp. R819-R829, Sep. 1994.

Krauchi et al., Circadian Clues to Sleep Onset Mechanisms, Neuropsychopharmacology, vol. 25, No. S5, pp. S92-S96, Nov. 2001.

Krauchi et al., Functional link between distal vasodilation and sleep-onset latency, Am. J. Physiol. Regulatory Integrative Comp. Physiol., 278(3), pp. R741-R748, Mar. 2000.

Krauchi et al., Warm feet promote the rapid onset of sleep, Nature, vol. 401, pp. 36-37, Sep. 2, 1999.

Krilowicz et al.; Regulation of posterior lateral hypothalamic arousal related neuronal discharge by preoptic anterior hypothalamic warming; Brain Res.; 668(1-2); pp. 30-38; Dec. 30, 1994.

Kumar et al.; Ambient temperature that induces maximum sleep in rats; Physiol. Behav.; 98(1-2); pp. 186-191; Aug. 4, 2009.

Kumar et al.; Ambient temperature-dependent thermoregulatory role of REM sleep; Journal of Thermal Biology; 37(5); pp. 392-396; Aug. 2012.

Kumar et al.; Warm sensitive neurons of the preoptic area regulate ambient temperature related changes in sleep in the rat; Indian J. Physiol. Pharmacol.; 55(3); pp. 262-271; Jul.-Sep. 2011.

Kumar; Body temperature and sleep: are they controlled by the same mechanism?; Sleep and Biological Rhythms; 2(2); pp. 103-124; Jun. 2004.

Lack et al.; The rhythms of human sleep propensity and core body temperature; J. Sleep Res.; 5(1); pp. 1-11; Mar. 1996.

Lee et al.; Thermal spot over human body surface (part 1) regional difference in cold spot distribution; J. Human and Living Environment; 2(1); pp. 30-36; 1995 (year of pub. sufficiently earlier than effective US filing date and any foreign priority date).

Leshner et al., Manifestations and Management of Chronic Insomnia in Adults, NIH State-of-the-Science Conference, Final Panel Statement, Bethesda, MD, 36 pgs., Jun. 13-15, 2005.

Libert et al.; Effect of continuous heat exposure on sleep stages in humans; Sleep; 11(2); pp. 195-209; Apr. 1988.

Lu et al.; Effect of lesions of the ventrolateral preoptic nucleus on NREM and REM sleep; J. Neurosci.; 20(10); pp. 3830-3842; May 15, 2000.

Mahapatra et al.; Changes in sleep on chronic exposure to warm and cold ambient temperatures; Physiol. Behav.; 84(2); pp. 287-294; Feb. 15, 2005.

McGinity et al.; Hypothalamic regulation of sleep and arousal; Frontiers in Bioscience; 8; pp. s1074-s1083; Sep. 1, 2003.

McGinity et al.; Keeping cool: a hypothesis about the mechanisms and functions of slow-wave sleep; TINS; 13(12); pp. 480-487 ; Dec. 1990.

McGinity et al.; Sleep suppression after basal forebrain lesions in the cat; Science; 160(3833); pp. 1253-1255; Jun. 14, 1968.

McKenzie/Mini-Mitter Co.; Mini-Logger® Series 2000, Physiological Data Logging Device; 510K Summary and Premarket Notification (No. K033534); 10 pgs.; Apr. 22, 2004.

Methipara et al.; Preoptic area warming inhibits wake-active neurons in the perifornical lateral hypothalamus; Brain Res.; 960(1-2); pp. 165-173; Jan. 17, 2003.

Morairty et al.; Selective increases in non-rapid eye movement sleep following whole body heating in rats; Brain Res.; 617(1); pp. 10-16; Jul. 16, 1993.

Nadel et al.; Differential thermal sensitivity in the human skin; Pflugers Arch.; 340(1); pp. 71-76; 1973 (year of pub. sufficiently earlier than effective US filing date and any foreign priority date).

Nakamura; Central circuitries for body temperature regulation and fever; Am. J. Physiol. Regul. Integr. Comp. Phsiol.; 301(5); pp. R1207-R1228; Nov. 2011.

Nakayama et al.; Thermal stimulation of electrical activity of single units of the preoptic region; Am. J. Physiol.; 204(6); pp. 1122-1126; 1963 (year of pub. sufficiently earlier than effective US filing date and any foreign priority date).

Nakayama; Single unit activity of anterior hypothalamus during local heating; Science; 134(3478); pp. 560-561; Aug. 25, 1961.

Nauta; Hypothalamic regulation of sleep in rats. An experimental study; J. Neurophysiol.; 9; pp. 285-316; Jul. 1946.

Nofzinger et al., Functional Neuroimaging Evidence for Hyperarousal in Insomnia, Am J Psychiatry, 161(11), pp. 2126-2128, Nov. 2004.

Nofzinger et al.; Alterations in regional cerebral glucose metabolism across waking and non-rapid eye movement sleep in depression; Arch. Gen. Psychiatry; 62(4); pp. 387-396; Apr. 2005.

Nofzinger et al.; Frontal cerebral hypothermia: A new approach to the treatment of insomnia; Sleep; Abstract Suppl.; vol. 32; abstract No. 0881; pp. A287-A288; Jun. 2009.

Nofzinger et al.; Frontal cerebral thermal transfer as a treatment for insomnia: A dose-ranging study; Sleep; Abstract Suppl.; vol. 34; abstract No. 0534; p. A183; Jun. 2011.

Nofzinger et al.; Regional cerebral metabolic correlates of WASO during NREM sleep in insomnia; J. Clinical Sleep Med.; 2(3); pp. 316-322; Jul. 2006.

Nofzinger/Cereve; SBIR/STTR Grant Submission; Feasibility of frontal cerebral hypothermia as a treatment for insomnia; submitted Dec. 9, 2008.

Obal et al.; Changes in the brain and core temperatures in relation to the various arousal states in rats in the light and dark periods of the day; Pflugers Arch.; 404(1); pp. 73-79; May 1985.

Olympic Medical; Olympic Cool-Cap System (Product Brochure); 4 pgs.; (year of pub. sufficiently earlier than effective US filing date and any foreign priority date) 2007.

Osborne et al.; Effects of hypothalamic lesions on the body temperature rhythm of the golden hamster; Neuroreport; 6(16); pp. 2187-2192; Nov. 13, 1995.

Parmeggiani et al; Hypothalamic temperature during the sleep cycle at different ambient temperatures; Electroencephalogr. and Clin. Neurophysiol.; 38(6); pp. 589-596; Jun. 1975.

Parmeggiani; Interaction between sleep and thermoregulation: an aspect of the control of behavioral states; Sleep; 10(5); pp. 426-435; Oct. 1987.

Parmeggiani et al.; Sleep and environmental temperature; Arch. Ital. Biol.; 108(2); pp. 369-387; Apr. 1970.

Poole et al.; Body temperature regulation and thermoneutrality in rats; Q. J. Exp. Physiol. Cogn. Med. Sci.; 62(2); pp. 143-149; Apr. 1977.

Ray et al.; Changes in sleep-wakefulness in the medial preoptic area lesioned rats: role of thermal preference; Behav. Brain Res.; 158(1); pp. 43-52; Mar. 7, 2005.

Ray et al.; Changes in thermal preference, sleep-wakefulness, body temperature and locomotor activity of rats during continuous recording for 24 hours; Behav. Brain Res.; 154(2); pp. 519-526; Oct. 5, 2004.

Raymann et al.; Diminished capability to recognize the optimal temperature for sleep initiation may contribute to poor sleep in elderly people; Sleep; 31(9); pp. 1301-1309; Sep. 2008.

Raymann et al.; Skin deep: enhanced sleep depth by cutaneous temperature manipulation; Brain; 131(Pt 2); pp. 500-513; Feb. 2008.

Reyner et al., Evaluation of 'In-Car' Countermeasures to Sleepiness: Cold Air and Radio, Sleep, vol. 21(1), pp. 46-50, (year of pub. sufficiently earlier than effective US filing date and any foreign priority date) 1998.

Romanovsky et al.; Molecular biology of thermoregulation selected contribution: ambient temperature for experiments in rats: a new method for determining the zone of thermal neutrality; J. Appl. Phsyiol.; 92(6); pp. 2667-2679; Jun. 2002.

(56) References Cited

OTHER PUBLICATIONS

Schmidek et al.; Influence of environmental temperature on the sleep-wakefulness cycle in the rat; Physiol. Behav.; 8(2); pp. 363-371; Feb. 1972.
Setokawa et al.; Facilitating effect of cooling the occipital region on nocturnal sleep; Sleep and Biological Rhythms; 5(3); pp. 166-172; Jul. 2007.
Sewitch; Slow wave sleep deficiency insomnia: a problem in thermo-downregulation at sleep onset; Phychophsyiology; 24(2); pp. 200-215; Mar. 1987.
Shapiro et al.; Thermal load alters sleep; Biol. Psychiatry; 26(7); pp. 736-740; Nov. 1989.
Sherin et al.; Activation of ventrolateral preoptic neurons during sleep; Science; 271(5246); pp. 216-219; Jan. 12, 1996.
Srividya et al.; Differences in the effects of medial and lateral preoptic lesions on thermoregulation and sleep in rats; Neuroscience; 139(3); pp. 853-864; 2006 (year of pub. sufficiently earlier than effective US filing date and any foreign priority date).
Srividya et al.; Sleep changes produced by destruction of medial septal neurons in rats; Neororeport; 15(11); pp. 1831-1835; Aug. 2004.
Sterman e tal.; Forebrain inhibitory mechanisms: sleep patterns induced by basal forebrain stimulation in the behaving cat; Exp. Neurol.; 6; pp. 103-117; Aug. 1962.
Stevens et al.; Regional sensitivity and spatial summation in the warmth sense; Physiol. Behav.; 13(6); pp. 825-836; Dec. 1974.
Stevens et al.; Temperature sensitivity of the body surface over the life span; Somatosens. Mat. Res.; 15(1); pp. 13-28; 1998 (year of pub. sufficiently earlier than effective US filing date and any foreign priority date).
Szymusiak et al.; Ambient temperature-dependence of sleep disturbances produced by basal forebrain damage in rats; Brain Res. Bull.; 12(3); pp. 295-305; Mar. 1984.
Szymusiak et al.; Maximal REM sleep time defines a narrower thermoneutral zone than does minimal metabolic rate; Physiol. Behav.; 26(4); pp. 687-690; Apr. 1981.
Szymusiak et al.; Sleep suppression following kainic acid-induced lesions of the basal forebrain; Exp. Neurol.; 94(3); pp. 598-614; Dec. 1986.
Szymusiak et al.; Sleep-related neuronal discharge in the basal forebrain of cats; Brain Res.; 370(1); pp. 82-92; Apr. 2, 1986.
Tamura et al.; Thermal spot over human body surface (part II) regional diference in warm spot distribution; J. Human and Living Environment; 2(1); pp. 37-42; 1995 (year of pub. sufficiently earlier than effective US filing date and any foreign priority date).
Thannickal et al.; Effect of ambient temperature on brain temperature and sleep-wakefulness in medial preoptic area lesioned rats; Indian J. Pharmacol.; 46(3); pp. 287-297; Jul. 2002.
Van Someren; Mechanisms and functions of coupling between sleep and temperature rhythms; Progress in Brain research; 153; pp. 309-324; 2006 (year of pub. sufficiently earlier than effective US filing date and any foreign priority date).
Van Someren; More than a maker: interaction between the ciradian regulation of temperature and sleep, age-related changes, and treatment possibilities; Chronobiol. Int.; 17(3); pp. 313-354; May 2000.
Von Economo; Sleep as a problem of localization; The Journal of Nervous and Mental Disease; 71(3); pp. 1-5; Mar. 1930.
Wang et al., Rapid and selective cerebral hypothermia achieved using a cooling helmet, Journal of Neurosurgery, vol. 100 No. 2, pp. 272-277 (full text version 18 pgs), Feb. 2004.
Yavuz et al.; Thermoelectric brain cooler helmet; 6th International Advanced Technologies Symposium (IATS'11); Elazig, Turkey; pp. 120-123; May 16-18, 2011.
Tucker et al., U.S. Appl. No. 15/921,528, entitled "Non-Invasive brain temperature regulating devices for enhancing sleep," filed Mar. 14, 2018.
Bonnet et al.; Heart rate variability: sleep stage, time of night and arousal influences; Electroencephalography and Clinical Neurophysiology; 102(5); pp. 390-396; May 1997.

Effects of treatment expectations on sleep latency

Effects of treatment expectations on sleep efficiency

APPARATUS AND METHOD FOR MODULATING SLEEP

CROSS REFERENCE TO RELATED APPLICATIONS

This patent claims priority as a Continuation under 35 U.S.C. § 120 of U.S. patent application Ser. No. 14/341,642, filed on Jul. 25, 2014, titled "APPARATUS AND METHOD FOR MODULATING SLEEP," now U.S. Pat. No. 9,211, 212, which claims priority a Continuation-in-Part under 35 U.S.C. § 120 to U.S. patent application Ser. No. 12/288,417, filed on Oct. 20, 2008, and titled "METHOD AND APPARATUS OF NONINVASIVE, REGIONAL BRAIN THERMAL STIMULI FOR THE TREATMENT OF NERUOLOGICAL DISORDERS," now U.S. Pat. No. 9,492,313, which is a Continuation-in-Part application and claims priority under 35 U.S.C. § 120 to patent application Ser. No. 11/788,694, filed on Apr. 20, 2007, and titled "METHOD AND APPARATUS OF NONINVASIVE, REGIONAL BRAIN THERMAL STIMULI FOR THE TREATMENT OF NEUROLOGICAL DISORDERS," now U.S. Pat. No. 8,236,038, which claims priority under 35 U.S.C. § 119(e) to U.S. Provisional Patent Application No. 60/793,680, filed on Apr. 20, 2006, and titled METHOD AND APPARATUS OF BRAIN COOLING FOR THE TREATMENT OF NEUROLOGICAL DISORDERS," each of which is herein incorporated by reference in its entirety.

U.S. patent application Ser. No. 14/341,642 also claims priority under 35 U.S.C. § 119(e) to U.S. Provisional Patent Application No. 61/859,161, filed on Jul. 26, 2013, and titled "APPARATUS AND METHOD FOR MODULATING SLEEP," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatus and methods described herein may be used to improve sleep, including reducing sleep onset, improving sleep maintenance, increasing sleep duration, and increasing deep sleep relative to light sleep in a subject, including subject suffering from a disorder that affects sleep such as insomnia. Thus, the apparatuses and methods described herein may be used to treat sleeping disorders such as insomnia.

BACKGROUND

Although sleep disruption and irregularities, including insomnia, are a widespread and pervasive problem, there are few systems for the treatment and/or enhancement of sleep. For example, previously described devices and techniques for the treatment of sleep disorders have included the use of cooling therapies, including cooling applied to a patient's forehead, to enhance sleep. This has been described, for example, in U.S. Pat. Nos. 8,425,583, and 8,236,038, each of which are herein incorporated by reference in their entirety. Thus, there is evidence for the enhancing sleep by cooling a subject's skin (e.g., forehead), perhaps by taking advantage of a mechanism involving cooling of underlying brain regions. This clinically demonstrated effect may suggest that warming (relative to ambient temperature), rather than cooling, the subject's forehead would have a generally deleterious effect on sleep. However, to date, research touching on the effects of applying higher temperatures to a subject's skin, and specifically a subject's forehead, is somewhat inconclusive.

In general, preclinical studies have suggested that the control of sleep and thermoregulation are integrated at the level of the hypothalamus. Human studies have shown that manipulation of environmental temperature by various means can impact on sleep, however it is not well understood how selective regions of the body can influence hypothalamic sleep and thermoregulatory centers. Clinical insomnia and sleeplessness in general are characterized by transient or chronic difficulty initiating and maintaining sleep though it has been unclear if alterations in thermoregulation play a significant role in the pathophysiology or treatment of the disorder. Physiological and neuroanatomical studies show that the forehead is a region of the body that has unique properties suggesting it may play a prominent role in impacting the hypothalamic control of thermoregulation and by extension may influence the hypothalamic thermoregulatory control of sleep.

Insomnia is most often described as the inability to fall asleep easily, to stay asleep or to have quality sleep in an individual with adequate sleep opportunity. In the U.S., population-based estimates of either chronic or transient insomnia range from 10 to 40% of the population, or 30 to 120 million adults in the United States. Similar prevalence estimates have been reported in Europe and Asia. Across studies, there are two age peaks: 45-64 years of age and 85 years and older. Women are 1.3 to 2 times more likely to report trouble sleeping than men, as are those who are divorced or widowed, and have less education. In the U.S., the economic burden of insomnia approaches $100 billion, in direct health care costs, functional impairment, increased risk of mental health problems, lost productivity, worker absenteeism and excess health care utilization. It is recognized as a public health problem, contributing to more than twice the number of medical errors attributed to health care workers without insomnia episodes. Currently available treatments for insomnia, however, are not entirely satisfactory for a variety of reasons. Sedative-hypnotics are not a complete solution to the problem of insomnia as they are associated with significant adverse events such as the potential for addiction/dependence, memory loss, confusional arousals, sleep walking and problems with coordination that can lead to falls and hip fractures. The majority of insomnia patients would prefer a non-pharmaceutical approach to their insomnia complaints. Cognitive behavior therapy, while effective, is an expensive and labor intensive treatment that is not widely available and is not always covered by health insurance. Over the counter approaches to the treatment of insomnia including a variety of medications and devices suffer from inadequate clinical studies demonstrating significant effects in insomnia patients, as well as potentially dangerous side effects. A large need exists, therefore, for a safe, effective, non-invasive, non-pharmaceutical device for the treatment of sleep including treatment of sleep disorders.

Recent advances have been made in the neurobiology of sleep and in the neurobiology of insomnia that can inform innovative treatments for insomnia. "Hyperarousal", on a variety of physiological levels, represents the current leading pathophysiological model of insomnia. The degree to which this hyperarousal is mediated by alterations in thermoregulatory control is unclear. Insomnia patients have been shown to have increased whole brain metabolism across waking and sleep in relation to healthy subjects; resting metabolic rate, heart rate and sympathovagal tone in HRV, cortisol secretion in the evening and early sleep hours, beta EEG activity during NREM sleep, increased levels of cortical glucose metabolism, especially in the frontal cortex, associated with higher levels of wakefulness after sleep onset, impairments in the normal drop in core body temperature around the sleep onset period; and cognitive hyperarousal resting on the pre-sleep thoughts of insomnia patients, often described as "racing," unstoppable, and sleep-focused. Insomnia patients have demonstrated increases in beta EEG spectral power that correlate with increased metabolism in the ventromedial prefrontal cortex during NREM sleep. Improvements in sleep in insomnia patients have been associated with improvements in prefrontal cortex function as measured by functional neuroimaging.

Considerable evidence suggests that sleep and thermoregulation are integrated at the level of the hypothalamus. Development of interventions designed to impact on these relationships may be fruitful in the design of interventions for the treatment of insomnia.

The induction, maintenance and timing of wake, non-rapid eye movement sleep (NREM) or slow wave sleep (SWS), and rapid eye movement (REM) sleep are the products of complex interactions among multiple structures and mechanisms which are widely distributed throughout the brain. Reciprocal interactions between sleep and wake promoting systems ensure that the behavioral state of sleep-wakefulness is altered as per requirement. Prominent among these sleep-promoting structures are the pontine tegmentum and adjacent neuronal groups involved in the generation of REM sleep features. On the other hand the NREM sleep is promoted by several areas including the medial preoptic area (mPOA), the lateral preoptic area (lPOA), the ventrolateral preoptic area (vlPOA), the median preoptic nucleus (mnPO), and the medial septum, which are referred to as basal forebrain (BF) areas (Sherin et al., 1996; John and Kumar, 1998; Gong et al., 2000; Lu et al., 2000; Srividya et al., 2004, 2006). There are external and internal factors that influence the swing of sleep-wakefulness toward either sleep or awake state. The BF plays a strategic role in integrating thermoregulation and sleep regulation.

Body temperature regulation is a fundamental homeostatic function that is regulated by the central nervous system. The preoptic area (POA, such as the mPOA, mnPOA, lPOA, vlPOA) is considered the most important thermoregulatory site in the brain on the basis of thermoregulatory responses elicited by local warming and cooling, lesion, stimulation and single neuronal recording, and many other techniques (Nakayama et al., 1961, 1963; Boulant and Hardy, 1974; Boulant, 1981; Boulant and Dean, 1986). The thermosensitive neurons in the POA receive and integrate cutaneous and deep body thermal information. These neurons are tonically active at thermoneutral temperature, and control the thermoregulatory efferent pathway (Nakayama et al., 1961, 1963).

The existence of sleep-wake promoting areas in the brain was first indicated by von Economo. Postmortem examination of the brains of Encephalitis lethargica patients with hypersomnolence showed that they had lesions at the junction of the midbrain and the diencephalon (von Economo, 1930). On the other hand, some patients with lesion in the anterior hypothalamic-POA (POAH) had insomnia. The concept of the POA as a sleep-promoting area and the posterior hypothalamus as the wake promoting area was supported by several lines of animal experiments employing stimulation, lesion, single unit recording, neural transplantation, functional magnetic resonance imaging (fMRI), and c-fos studies (Nauta, 1946; Sterman and Clemente, 1962; McGinty and Sterman, 1968; Szymusiak and McGinty, 1986; John et al., 1994, 1998; Sherin et al., 1996; John and Kumar, 1998; Khubchandani et al., 2005). Clinical evidence and experimentations over the last 80 years have led to the prevailing hypothesis that BF has SWS promoting or hypnogenic structures. More recently, sleep active neurons have been found to be concentrated in the vlPOA and mnPO (Gong et al., 2000; Lu et al., 2000). The importance of these cell groups is evident from c-fos expression during sleep state (Sherin et al., 1996).

To study the neural mechanism involved in the regulation of sleep, temperature and their interrelation we depend on the information obtained from lower animals. In cats, sleep was maximal at thermoneutral zone (TNZ) and that it decreases above and below TNZ (Parmeggiani et al., 1969). Subsequently several reports showed that the ambient temperature (T) produces complex changes in both NREM/SWS and REM sleep. The changes in sleep-wakefulness were studied in rats when they were exposed to different ambient temperature of 18, 24, and 30° C. (Thomas and Kumar, 2000). There was an increase in REM sleep and SWS, and a decrease in wakefulness at higher ambient temperature of 30° C. Even chronic exposure to 30° C. produced persistent increase in REM sleep (Mahapatra et al., 2005). According to one report on rats, NREM sleep and the metabolic rate were not affected much in between 23 and 31° C. However, the amount of REM sleep was at its peak at 29° C., and a marked decrease occurred at 33° C. (Szymusiak and Satinoff, 1981). Exposure of rats to gradual increase in ambient temperature from 18 to 30° C. produces a linear increase in the percentage of REM sleep (Szymusiak and Satinoff, 1984; Thomas and Kumar, 2000; Kumar et al., 2009). The increase in the amount of sleep may be considered as an adaptation to thermal load aimed at energy conservation (Obal et al., 1983). When human subjects were exposed to a range of ambient temperature, total sleep time (TST), NREM, and REM sleep were maximal at 29° C. (Haskell et al., 1981). But when they were exposed to T of 35° C., there was fragmented sleep with decrease in TST and increase in wakefulness, without any change in REM or delta sleep (Libert et al., 1988). Sleep is reduced when the T is lowered (Parmeggiani and Rabini, 1970; Schmidek et al., 1972; Szymusiak and Satinoff, 1984; Alföldi et al., 1990; Rosenthal and Vogel, 1991; Ray et al., 2004). The TST, SWS, and REM sleep are decreased in rats when they are exposed to T of 18±1° C. for a few hours (Thomas and Kumar, 2000; Mahapatra et al., 2005). It was suggested that the central nervous system calls for an increase in the amount of arousal, at the expense of the sleep stages, especially REM sleep, in order to maintain the body temperature (T) when the T is low (Parmeggiani and Rabini, 1970; Alföldi et al., 1990). An increase in arousal in cold T is necessary for the production of more heat (Schmidek et al., 1972; Parmeggiani et al., 1975).

As sleep is said to be influenced by T and the REM sleep is said to vary within the TNZ, it is important to address the question of TNZ for small animals. The most widely used method to study TNZ, i.e., minimum metabolic rate, has found the TNZ to be between 18 and 28° C. (Poole and Stephenson, 1977). Many others have described a range of 28-34° C. (Herrington, 1940; Clarkson et al., 1972; Gordon, 1987). According to another definition, the TNZ is "the range of T at which temperature regulation is achieved only by control of sensible heat loss." Based on this the TNZ for Wistar rats have been reported to be between 29.5 and 30.5° C. (Romanovsky et al., 2002). Thus the suggested TNZ from all these studies vary from 18 to 34° C. Such contradictions described above emphasize that the TNZ for a given species, as determined by using a particular technique, is of little help in selecting the T for another study using a different variable. Therefore, before determining the responses to T on sleep, it makes sense to determine the TNZ of the animal using the behavioral criteria. Three different sets of temperatures (first set: 18, 24, and 27° C.; second set: 24, 27, and 30° C.; and third set: 27, 30, and 33° C.) were employed to study the thermal preference while looking into the influence of T on sleep architecture. It was found that the rats preferred to stay at 27° C., while the maximum sleep was obtained at 29-30° C. (Ray et al., 2004, 2005; Kumar et al., 2009, 2012). Sleep-wakefulness recordings during the day time in the nocturnal rats showed that the sleep followed a bell-shaped distribution, with a maximum during 11:00-15:00 hours (FIG. 2). The T, on the other hand, showed a reversed bell-shaped curve. The trough of T curve could be attributed to diurnal influence and sleep-related change (Obal et al., 1985; Alföldi et al., 1990; Baker et al., 2005). The T trough disappeared at 30° C., though maximal REM sleep was recorded at the T of 30° C. The increased sleep at around the T of 30° C. may be a response to thermal load aimed at energy conservation (Obal et al., 1983). It was seen that the increase in thermal load at 30° C. attenuated the diurnal lowering of T. The ability to oppose diurnal shift in the T resides in the POA, as the lesion of this area produced higher diurnal change in the T in golden hamsters (Osborne and Refinetti, 1995). The POA could be involved in fine-tuning the body temperature to regulate sleep as per the requirement (Thomas and Kumar, 2002; Kumar, 2005). Though the maximum sleep was recorded at 30° C., the thermoregulatory diurnal oscillation was least disturbed only at 27° C. T.

These studies in rats suggest that sleep can be modulated by subtle changes in ambient temperature and raise the possibility that even minor changes in ambient temperature may influence sleep in significant manners.

Stimulation of central thermoreceptors by circulating blood temperature is likely to be an important source of impulses driving sleep inducing structures of BF (Moruzzi, 1972). Body and brain temperatures of rats are increased by more than 1° C. when the ambient temperature is increased from 21 to 29° C. (Alfoldi et al., 1990). This increase in body and brain temperatures may be responsible for the increase in SWS/NREM in animals and human subjects at warm T (Horne and Staff, 1983; Horne and Shackell, 1987; Shapiro et al., 1989; McGinty and Szymusiak, 1990; Morairty et al., 1993). This possibility is supported by the observation that local warming of the POA using chronically implanted water perfused thermode triggered SWS or EEG slow wave activity in rats, rabbits, and cats (McGinty and Szymusiak, 2003). Delta activity is also increased during this sustained SWS. Sustained increase in delta activity supports a hypothesis that sleep drive is modulated by thermosensitive neurons of the POA. On the other hand, both SWS and REM sleep were suppressed by mild cooling of the POA. Warm sensitive neurons (WSN) and cold sensitive neurons (CSN) have been identified in the POA on the basis of in vivo and in vitro studies (Nakayama et al., 1961, 1963). These neurons are identified on the basis of responses to local warming or cooling. Most WSN are sleep active, whereas CSN are wake active. The activities of posterior hypothalamic neurons, dorsal raphe in the midbrain, lateral hypothalamic orexinergic neurons, and BF cholinergic neurons are inhibited by the POA warming (Krilowicz et al., 1994; Alam et al., 1995a; Guzman-Marin et al., 2000; Methipara et al., 2003). These findings suggest the possibility that the WSN of the POA do have an inhibitory action on the arousal promoting neurons. Results from the POA warming studies indicate a homeostatic regulation by which sleep is promoted during mild rise of body temperature, which not only plays a thermoregulatory role but also serves as a protective mechanism to prevent the animal from venturing into a hostile thermal environment.

Based on the results of several studies it is concluded that both ambient and body temperatures profoundly influence sleep architecture (Horne and Staff, 1983; Obal et al., 1983; Szymusiak and Satinoff, 1984; Horne and Shackell, 1987; Shapiro et al., 1989; McGinty and Szymusiak, 1990; Morairty et al., 1993; Thomas and Kumar, 2000; Kumar et al., 2009). The thermoregulatory pathway which initiates heat and cold defense response is conveyed by skin thermoreceptors, en route dorsal horn, and parabrachial nuclei, to the POA (Nakamura, 2011). It is natural to assume that changes in sleep brought about by T is sensed and mediated by thermoreceptors. The roles of peripheral and central thermoreceptors have been investigated in order to get an insight into the role of afferent thermal inputs, from periphery and core, in the promotion of sleep. Capsaicin has been traditionally used for destruction of thermoreceptors and WSN. In an earlier report, sleep-wakefulness was studied in normal and capsaicin-treated rats when they were placed at T of 22 and 29° C. (Obal et al., 1983). There was an increase in sleep at the elevated temperature of 29° C., though REM sleep showed only a minor increase. The ambient temperature related increase in NREM sleep was not seen after destruction of peripheral and central warm receptors. There are different experimental models to explore the relative role of peripheral and central thermoreceptors in the T mediated sleep mechanism. In the first model, systemic administration of capsaicin in high doses destroys both peripheral and central warm receptors. In the second model, local application in the POA destroys WSN in this region only. In the third model, when neonatal rats are treated with capsaicin, their peripheral thermosensitivity is lost, while their central thermoregulatory neurons are preserved (Hajos et al., 1983). As mentioned earlier, when the rats were exposed to 27, 30, and 33° C., the rats had maximum sleep at 30° C., though they preferred to stay at 27° C. When both peripheral and central warm receptors, were destroyed in these rats (by systemic administration of capsaicin), the selective increase in REM sleep at 30° C. was not seen (Kumar et al., 2012). When peripheral warm receptors were selectively destroyed by neonatal treatment of capsaicin, the central warm receptors were able to mediate an increase in TST with increasing T, even in the absence of peripheral warm receptors (Gulia et al., 2005). This shows that the central WSN mediate the warm T related increase in SWS and REM sleep. When WSN of the POA were destroyed by local injection of capsaicin, the increase in REM sleep and SWS at 30° C. was not observed. SWS peak was brought down to 27° C., and REM sleep peak shifted to a higher temperature of 33° C., in these animals. The study clearly indicates that WSN of the POA mediate the increase in SWS, at temperatures higher than preferred T. The study shows that the neurons of the POA play a key role in regulating sleep as per homeostatic requirement (Kumar et al., 2011).

Much attention has been given to the physiological role of the POA, because of its ability to control thermoregulation and sleep. Many of the observations cited earlier support the hypothesis that sleep is modulated by thermosensitive neurons of the POA (Parmeggiani et al., 1975; Obal et al., 1983; McGinty and Szymusiak, 1990). Although this relationship has drawn considerable interest, it is still not known whether there is a "cause and effect" relationship or whether these changes are merely coincidental. Single unit studies clearly demonstrate that the POAH neurons, likely to be responsible for thermoregulation, are influenced by vigilance states (Alam et al., 1995a). The thermosensitivity of the POA neurons are reduced during SWS as compared to wakeful state (Parmeggiani et al., 1987). During SWS, a majority of WSN of POAH exhibit increased discharge rate. CSN exhibit less discharge during SWS and decreased thermosensitivity. The activation of these sleep-related WSN and inhibition of wake related CSN may play a role in the onset and regulation of SWS (Alam et al., 1995b). It could also be assumed that the POAH neurons which are responsible for sleep-wake modulations are thermosensitive (Szymusiak and McGinty, 1985; McGinty and Szymusiak, 2003). Most of the assertions that thermoreceptive elements control sleep regulation are based on results obtained from warming and cooling of the POAH neurons using thermodes. Warming of the POAH has been shown to suppress activity in the wake related magnocellular BF and posterior lateral hypothalamus of cats (Krilowicz et al., 1994; Alam et al., 1995a,b) and dorsal raphe and lateral hypothalamus of rats (Guzman-Marin et al., 2000; Methipara et al., 2003). These results suggest that WSN of the POAH may play a key role in the regulation of SWS sleep (Alam et al., 1995a,b; McGinty and Szymusiak, 2003). So, the modulation of sleep-wake state by POAH thermosensitive neurons must be viewed as a distinct possibility.

The influence of diurnal temperature rhythm on sleep is best studied in man. Both skin temperature and core body temperature show a day-night rhythm. In humans, the core temperature is relatively low during sleep at night and it is relatively high during waking period during day time. Skin temperature also exhibits a circadian rhythm, but its changes are reciprocal to that of the core body temperature rhythm (van Someren, 2006). The core body temperature and sleep propensity are negatively related, whereas skin temperature and sleep are positively related (Magnussen, 1939; Lack and Lushington, 1996). The degree of heat loss at the skin of the hands and feet is said to be the best physiologic predictor for a rapid sleep onset (Kräuchi et al., 1999, 2000). It was suggested that autonomous thermoregulatory changes in core body temperature and skin temperature could act as an input signal to modulate neuronal activity in sleep-regulating brain areas (van Someren, 2000). The activities of thermosensitive neurons in the POAH, are suggested to be modulated more strongly by changes in skin temperature, than by changes in core temperature (Boulant and Bignall, 1973). Manipulation of the skin temperature across the entire body within the TNZ can modulate sleepiness and sleep depth, even without activating thermoregulatory responses (Raymann et al., 2008). Even mild changes in skin temperature that occur during normal sleep can have an effect on sleep propensity not only in young adults but also in elderly subjects (Raymann and Van Someren, 2008). It remains unclear however if there are specific regions of the body that are most responsible for providing afferent thermal information to the POAH. The prior art teaches that the hands and feet may play a key role in the transmission of thermal information though it does not describe other body parts as significantly influencing these interactions.

Some studies support alterations in thermoregulation in insomnia patients. For example, one component of "hyperarousal" in insomnia that has been investigated as part of the pathophysiology of the disorder is an abnormal thermoregulation in insomnia patients. In healthy sleepers, there is a normal decline in core body temperature that occurs at sleep onset and continues throughout a night of sleep. Sewitch (1987) described abnormal elevations in core body temperature in insomnia patients and suggested that slow wave sleep deficiencies in insomnia is the result of a failure to down regulate temperature at the beginning of the night. Compared to controls, insomniacs are reported to have higher oral pre-sleep onset temperatures and, under ad lib sleep conditions, both higher rectal and oral temperatures over the sleep period. Finally, consistent with the inverse relationship reported between core body temperature and distal peripheral temperature, insomniacs are also reported to have lower finger temperatures in the minutes prior to sleep onset. By contrast, two studies reported no difference between insomniacs and controls in core body temperature and other correlates of arousal. Adam et al. observed no significant difference under ad lib sleep conditions in either post-sleep onset oral temperature or daytime adrenocortical activity in middle-aged to elderly insomniacs compared to controls. Similarly, Freedman and Sattler observed no difference in a variety of autonomic activity measures (e.g., EMG, heart rate, finger temperature) between young sleep onset insomniacs and controls during ad lib sleep. However, it is to be noted in both cases that the trends were in the expected direction. Despite evidence of an association between physiological arousal and insomnia it is noteworthy that the majority of studies have measured arousal under ad lib sleep conditions. This methodological limitation may account for some of the group differences reported between insomniacs and controls. For example, group differences in physical activity and posture rather than sleep quality may account for temperature differences. Similarly, core temperature may be elevated in insomniacs compared to controls during ad lib sleep conditions simply because temperature is elevated during wakefulness and by definition insomniacs spend a greater period of the night awake. In brief, it could be argued that elevated core body temperature is simply a result of sleep-wake state rather than an endogenous contributor to insomnia as the hyper-arousal model would suggest. More direct evidence that core body temperature is elevated in insomniacs has come from work by one group where they examined temperature under wakeful constant routine conditions. They found that aged insomniacs (primarily sleep maintenance insomniacs) compared to controls had higher core body temperatures prior to their habitual sleep onset time at home and that this persisted across the wakeful constant routine night until early morning when both groups converged and showed similar core temperature values across the remainder of the day. These findings suggest that aged sleep maintenance insomniacs are not chronically hyper-aroused across the 24-h period but are endogenously hyper-aroused at night. One other study of core temperature evaluated in a constant routine protocol failed to find differences between good sleepers and insomniacs during the day or at night. Whether this lack of difference arose from the use of a younger age group or smaller differences in objective sleep parameters between groups needs further investigation. The cumulative evidence provides some support for elevated core body temperatures in insomnia suggesting that thermoregulation may play an important role in the pathophysiology and perhaps treatment of insomnia.

The first study to investigate the skin temperatures of insomniacs attempting sleep was conducted in 1979 by Brown who found that insomniacs did show increases in toe skin temperature when attempting sleep, but that sometimes there was no observable change. Yet, when toe temperature increases were observed, they were more variable, and took twice as long to reach the same amount of temperature change compared to good sleepers. Freedman and Sattler found that compared to good sleepers insomniacs have significantly lower finger skin temperatures from lights out through to Stage 2 sleep onset. However, it appears that once sleep is achieved, differences in distal skin temperatures between insomniacs and good sleepers disappear, suggesting a critical period between lights out and sleep onset. It is worth noting that Freedman and Sattler found their insomniacs scored significantly higher on measures of general anxiety and worry compared to good sleepers, providing support for a link between anxiety, insomnia and lower distal skin temperature More recent attempts to investigate the notion that insomniacs have attenuated distal skin temperature increases when attempting sleep have found conflicting results. Other research confirmed that middle-aged insomniacs with sleep onset and maintenance difficulties reported both higher levels of general anxiety and sleep anticipatory anxiety in their home environments compared to good sleepers. Surprisingly though, the rapid increases in finger temperature of the insomniacs were found to be greater than those of good sleepers when they were falling asleep. However, it should be noted that in the laboratory the insomniacs fell asleep as quickly as the good sleepers and, in that sense, were not displaying their characteristic insomnia. The insomniacs did have significantly higher core body temperatures (by approximately 0.2-1 C) throughout the circadian rhythm thus supporting the chronic hyper-arousal theory for those suffering combined sleep onset and sleep maintenance insomnia. It would have been of interest for this study to have measured proximal skin temperature, as, along with core temperature, it would be likely to be higher in the insomniacs prior to the sleep attempt. If so, this would produce a lower distal/proximal skin temperature gradient associated with longer sleep latencies in normal sleepers. However, such a result would not negate the finding of a robust increase of distal skin temperature when insomniacs fell asleep. The chronically higher core temperature also suggests that there was a greater need for the insomniacs to lose core heat via the fingers and they appeared able to do so in the laboratory free of their previous insomnia symptoms. On the other hand, a recent study by van den Heuvel et al. suggested that insomniacs have less ability to vasodilate in distal skin. They found that younger sleep onset insomniacs had no greater finger temperature increase when challenged by a warm (45° C.) contralateral hand bath than a neutral bath (30-35° C.), whereas good sleepers showed a greater increase to the warm bath. However, because the baseline finger temperatures were not reported, it is not possible to rule out the possibility that the attenuated response in the insomnia group was due to a ceiling effect in their finger temperature. Regardless of whether insomniacs show attenuated vasodilation responses, it is still relevant, at least from a clinical perspective, to investigate whether skin warming would facilitate sleep onset. Raymann et al. have recently found that foot (distal) skin warming significantly facilitated shorter sleep onsets in young and elderly healthy sleepers, but not significantly in sleep disturbed elderly. Interestingly though, this elderly insomnia group showed the greatest slowing of reaction speed during proximal skin warming. Therefore, in good sleepers, and possibly in insomniac's skin warming seems conducive to sleepiness which is consistent with the earlier suggested link between warm sensitive and sleep inducing neurons in the hypothalamus. However, as in the two previous studies this one was also conducted in the laboratory during the day without insomnia evident according to their relatively short sleep latencies.

Notably, studies of skin temperature in insomnia patients have focused on distal skin temperatures in the feet and hands. Whether there are other more temperature sensitive regions of the body that can transmit temperature sensitive information to the POAH is not known.

So, while the relationships between skin temperature and sleep have been reported, the impact of selectively altering temperature at select skin regions aside from the feet and hands has not been clarified. Further, selective changes in these regions in the treatment of sleeplessness or insomnia have not been described.

Among body regions, the forehead has unique physiological and neuroanatomical properties that suggest it may play a prominent role in influencing the thermoregulatory hypothalamic modulation of sleep. The distribution of warm and cold spots has been shown to be highest over the face and forehead of all body parts (Lee and Tamura 1995; Rein 1925; Strughold and Porz 1931; Tamura and Lee 1995). Thermal sensation has been shown to be highest in the forehead of all body parts. In one study (Nadel et al 1973), thermal irradiation was applied to selected skin areas to determine whether particular areas demonstrate a greater thermal sensitivity than others in determination of a physiological thermoregulatory response. Modifications in thigh sweating rate were related to the change in temperature of the irradiated skin and the area of skin irradiated by computing a sensitivity coefficient for each skin area. Thermal sensitivity of the face, as measured by its effect on sweating rate change from the thigh, was found to be approximately three times that of the chest, abdomen and thigh. Lower legs were found to have about one-half the thermal sensitivity of the thigh. Other studies have reported that thermal sensitivity is highest in the face of all body areas (Crawshaw et al 1975; Stevens and Choo 1998; Stevens et al 1974). Further, the forehead comprising glabrous (non-hairy) skin has been shown to play a prominent role in the body response to thermoregulation given that the heat transfer function and efficacy of glabrous skin is unique within the entire body based on the capacity for a very high rate of blood perfusion and the novel capability for dynamic regulation of blood flow (Hensley et al 2013).

These lines of evidence support the concept that application of a warming stimulus at the scalp on the forehead may be associated with improvements in sleep in insomnia patients via transmission of temperature sensitive information to the POAH. A medical device that alters skin temperature on the forehead, therefore, may be a very sensitive and non-invasive manner to regulate sleep in insomnia patients within a very narrow temperature range.

SUMMARY OF THE DISCLOSURE

Described herein are apparatuses and methods, including methods of using the apparatus to enhance sleep, reduce sleep onset latency, extend sleep duration and/or increasing the duration of deeper sleep stages relative to stage 1 sleep. In general, these apparatuses and methods apply and maintain one or more target "warm" temperatures to a subject's forehead for a time period. The target temperature may be between 25° C. and 42° C. (including, e.g., 27° C.-40° C., 30° C.-40° C., 32° C.-40° C., 34° C.-40° C., such as 27° C., 28° C., 29° C., 30° C., 31° C., 32° C., 33° C., 34° C., 35° C., etc.). The target temperature may generally be a fixed amount greater than ambient temperature (but, in some variations, less than 40° C.). The time period may be a fixed time period or a variable time period. Generally, the time period is more than 15 minutes, more than 30 min, more than 1 hour, more than 2 hours, more than 3 hours, more than 4 hours, more than 5 hours, more than 6 hours, more than 7 hours, or more than 8 hours. For example, the time period may be 30 min, 1 hour, 2 hours, 3 hours, 4 hours, 5, hours, 6 hours, 7 hours, or 8 hours. The time period may be long enough to cover an entire sleep period for the subject. In some variations, the apparatus and/or method may be configured to apply multiple periods of fixed (and different) temperatures. For example, the apparatus may provide a treatment regime that includes initially applying warming above ambient temperature at a first temperature (e.g., between about 25° C.-40° C., such as 30° C.) for a first time period (e.g., 1 hour), then increasing temperature to a second temperature (e.g., between about 25° C.-40° C., such as 32° C.) for a second time period (e.g., 2 hours or more). Additional temperatures and time intervals may be applied. As discussed below, these different treatment regimes may modulate the subject's sleep patterns, including reducing sleep onset latency (due to the initial time and temperature) and reducing type 1 sleep ("light" sleep) relative to later ("deep") sleep stages.

For example, described herein are methods of enhancing sleep in a patient. In some variations, the method includes: positioning an applicator having a thermal transfer region so that the thermal transfer region contacts the subject's forehead, wherein the thermal transfer region does not contact the perioribtal, or cheek regions of the subject's face; and maintaining the temperature of the thermal transfer region at a target temperature that is warmer than ambient temperature while the subject is sleeping to enhance the subject's sleep.

As used herein, enhancing sleep may refer to one or more of: increasing the length/duration of sleep (e.g., staying asleep longer, etc.), reducing sleep latency/sleep onset, increasing the depth of sleep (e.g., increasing the time in deep sleep states, such as stage 3 sleep, and/or achieving deeper stage sleep, such as increasing the duration of deeper sleep stages relative to stage 1 sleep), and improving the subjective experience of sleep. The subjective experience of sleep may include self-reported quality of sleep indicators; for example, improving the subjective experience of sleep may include individual self-reported improvements in sleep. Thus, enhancing sleep is broadly intended to include both objective (e.g., EEG measurable data) as well as subjective (e.g., self-reported) indicators.

In general, the applicators described herein may be configured to limit the region of the body to which thermal energy is applied by the applicator. This may be achieved by configuring the thermal transfer region of the applicator so that it applies thermal energy (e.g., warming) to the forehead but does not provide a substantial amount of energy to other, non-forehead regions of the face. In general, the thermal transfer region may avoid applying energy to the eye orbit region (e.g., the region beneath the eyebrows, including the perioribtal and cheek regions of the face. The thermal transfer region may also be configured so that, when worn by the subject, it does not deliver a substantial amount of thermal energy to the non-facial portions of the head (such as the top and back of the head). Thus, the thermal transfer region may be configured to contact only the forehead (below the hairline or scalp in many subjects). Limiting the region of the face/head over which thermal energy is to be delivered directly in this manner may improve the comfort and effect of the apparatus and method, and may reduce the amount of energy required for treatment. As used herein the forehead may refer to the region of the head above the supraorbital ridge (above the eyes) and on either side by the temporal ridge (that links the supraorbital ridge to the coronal suture); and upper boundary of the forehead is typically the hairline.

In some variations, the system includes a disposable component and a reusable component. For example, the applicator may generally be reusable, but the skin-contacting (interface) portion of the thermal applicator may be configured to be used once or a few times and then replaced. Thus, the apparatus may include a disposable interface. Any of the methods of treatment described herein may therefore include a step of placing a disposable interface on the applicator before positioning the applicator, wherein the disposable interface forms at least a part of the thermal transfer region and is configured to contact the patient's forehead. The disposable interface may cover all or part of the applicator, or it may have an adhesive or other securement to hold it to the applicator so that it contracts the skin.

As mentioned, the step of positioning the applicator may include positioning the thermal transfer region so that the thermal transfer region does not contact the top or back of the subject's head. The step of positioning the applicator may comprise positioning the thermal transfer region only against the subject's forehead.

In general, maintaining the temperature of the thermal transfer region may comprise maintaining the temperature at a target temperature that is between about 25° C. and about 40° C. In some variations, maintaining the temperature of the thermal transfer region comprises maintaining the temperature at a target temperature that is at least about 0.5° C. greater than ambient temperature but is less than about 40° C. In some variations, maintaining the temperature of the thermal transfer region comprises maintaining the temperature at a target temperature for at least about 1 hour, for at least about 4 hours, and/or at a target temperature for the subject's entire sleep period.

Also described herein are methods of enhancing sleep in a patient, the method comprising: placing a disposable interface on an applicator, wherein the disposable interface forms at least a part of a thermal transfer region of the applicator and is configured to contact the patient's forehead; placing the thermal transfer region of the applicator against the subject's forehead; and maintaining the temperature of the thermal transfer region at a target temperature that is warmer than ambient temperature by at least 0.5° C. and is less than about 40° C., for at least a predetermined amount of time (for example, at least 15 minutes, at least 20 minutes, at least 30 minutes, at least 40 minutes, at least 45 minutes, at least one hour, at least 1.5 hours, at least 2 hours, at least 2.5 hours, at least 3.0 hours, etc.).

As mentioned, any of these methods may include placing the thermal transfer region of the applicator so that the thermal transfer region only contacts the subject's forehead, and/or so that the thermal transfer region does not contact the perioribtal, or cheek regions of the subject's face.

Also described herein are methods of decreasing sleep onset latency, the method comprising: positioning an applicator on the forehead of an awake subject so that a thermal transfer region of the applicator contacts the subject's forehead, wherein the thermal transfer region does not contact the perioribtal, or cheek regions of the subject's face;

preparing the patient to sleep; and reducing sleep onset latency by maintaining the temperature of the thermal transfer region at a target temperature that is warmer than ambient temperature for at least 30 minutes.

As described above, maintaining the temperature of the thermal transfer region may comprise maintaining the temperature at a target temperature that is between about 25° C. and about 40° C., maintaining the temperature at a target temperature that is at least about 0.5° C. greater than ambient temperature but is less than about 40° C., etc. The temperature may be maintained at a target temperature for at least about 1 hour, at least about 4 hours, and/or for the subject's entire sleep period.

Also described herein are methods of decreasing sleep onset latency, the method comprising: placing a disposable interface on an applicator, wherein the disposable interface forms at least a part of a thermal transfer region of the applicator and is configured to contact the patient's forehead; positioning an applicator on the forehead of an awake subject so that the thermal transfer region contacts the subject's forehead; and reducing sleep onset latency by maintaining the temperature of the thermal transfer region at a target temperature that is warmer than ambient temperature for at least 30 minutes.

Also described herein are methods of increasing sleep duration, the method comprising: positioning an applicator on the forehead of a subject so that a thermal transfer region of the applicator contacts the subject's forehead, wherein the thermal transfer region does not contact the perioribtal, or cheek regions of the subject's face; and increasing sleep duration by maintaining the temperature of the thermal transfer region at a target temperature that is warmer than ambient temperature for at least 1 hour while the subject is sleeping. The method of claim 23, further comprising placing a disposable interface on the applicator before positioning the applicator, wherein the disposable interface forms at least a part of the thermal transfer region and is configured to contact the patient's forehead.

Apparatuses capable and/or configured to perform these methods are also described. For example, an apparatus for enhancing sleep by decreasing sleep onset latency, increasing sleep duration, and/or increasing the duration of deeper sleep stages relative to stage 1 sleep, may include: an applicator configured to be worn over a subject's forehead, the applicator comprising a thermal transfer region configured to contact the subject's forehead but not to the perioribtal, or cheek regions of the subject's face; a thermal regulator unit comprising a thermal regulator (e.g., heater and/or cooler) and a controller for controlling the thermal regulator, wherein the thermal regulator is in thermal communication with the thermal transfer region; further wherein the controller is configured to control the temperature of the thermal regulator so that the thermal transfer region is maintained at a target temperature that is warmer than ambient temperature for greater than 30 minutes.

In some variations, the apparatus is configured so that the thermal transfer region only contacts the forehead.

The thermal regulator unit generally includes a heater and a controller for controlling the heater to regulate the temperature (by heating and/or cooling) of the thermal transfer region. A thermal regulator unit may include a thermal transfer medium that is heated/cooled to control the temperature of the thermal transfer region. For example the thermal regulator may include a thermal transfer medium forming part of the thermal transfer region. In some variations the thermal regulatory unit includes a thermal transfer medium comprising a thermal transfer fluid pumped through a transfer line of the thermal applicator. In some variations, the heater of the thermal regulator unit comprises a joule heating element. The apparatus may also include one or more temperature sensors, such as a temperature sensor operably connected to the sensor and configured to determine ambient temperature.

As used herein a "heater" is intended to include any appropriate source of thermal energy the temperature of which may be controlled by a controller. Thus, a "heater" may include both heating and cooling elements. A heater therefore is a portion of a thermal regulator unit that is configured to warm and/or cool a material that is in thermal communication with (or forms a part of) the thermal transfer region. As mentioned, a thermal regulator may be configured to cool as well as heat in order to regulate the temperature of the thermal transfer region. Thus the heater of the thermal regulator unit may include both heating (e.g., joule heating, chemical heating, etc.) and cooling (including any appropriate cooling mechanism, such as Peltier cooling, cooling fans, evaporative cooling, etc.) elements. Other exemplary heating/cooling ("heater" or "thermal engine") elements are described herein.

In general, the controller may be configured to control the temperature of the heater so that the thermal transfer region is maintained at a target temperature that is between about 25° C. and 40° C. for a time period. The time period may be predetermined or open ended. For example, the controller may be configured to turn "on" the device (while the user manually turns it off, or it may automatically turn off after a predetermined period of time, or because it is removed from the subject). For example, the controller may be configured to maintain the target temperature for more than 1 hour, 2 hours, or more. The apparatus may also include one or more controls (e.g., buttons, switches, etc.), including user controls that allow it to be activated or programmed.

BRIEF DESCRIPTION OF THE DRAWINGS

FIG. 4 show a significant decrease in sleep onset latency (the time to fall to sleep) when regulating forehead (and only forehead) temperature to 30° C.

FIG. 5 shows a significant increase in sleep efficiency in the same subjects, due to a dramatic increase in time asleep, as shown in FIG. 6.

FIG. 7 illustrates the percent change in stage 1 sleep in the same subjects examined in FIGS. 4-6.

FIGS. 8, 9 and 10 illustrates the percent change in stage 2 sleep, stage 3 delta sleep, and REM sleep, respectively, compared to baseline in the same subjects of FIGS. 4-7.

FIG. 11 summarizes the change in sleep stage dynamics and total sleep time in these patients.

FIG. 12 shows an improvement in the subjective quality of subject's sleep when regulating the temperature of the subject's forehead to 30° C. during and shortly before sleep. This effect appears to be independent of patient bias or expectation, as shown in FIGS. 13A and 13B, showing equivalent effects of 30° C. treatment in patients who both expected the cooling therapy to be effective (N=47) an those who did not expect the cooling therapy to be effective (N=41).

DETAILED DESCRIPTION

Figure 1A:
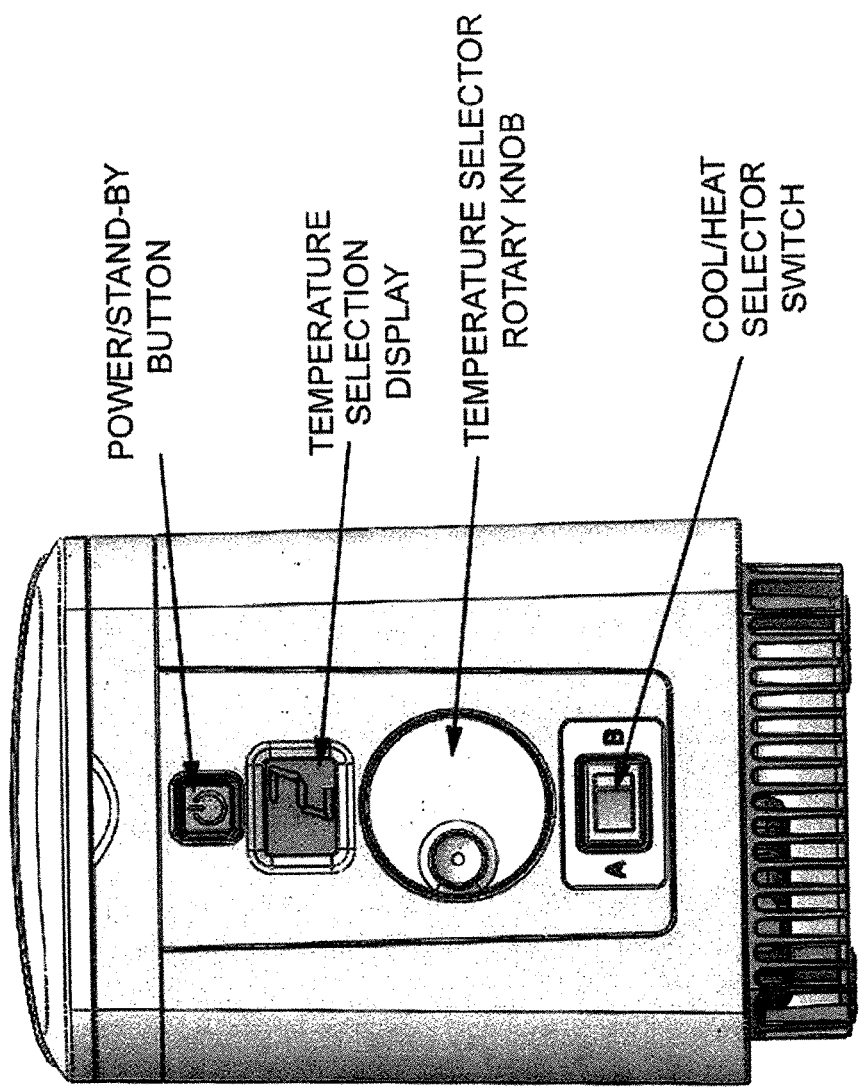
FIGS. 1A-1J illustrate one variation of a portion of an apparatus for enhancing sleep by increasing forehead temperature relative to ambient temperature.
Figure 1B:
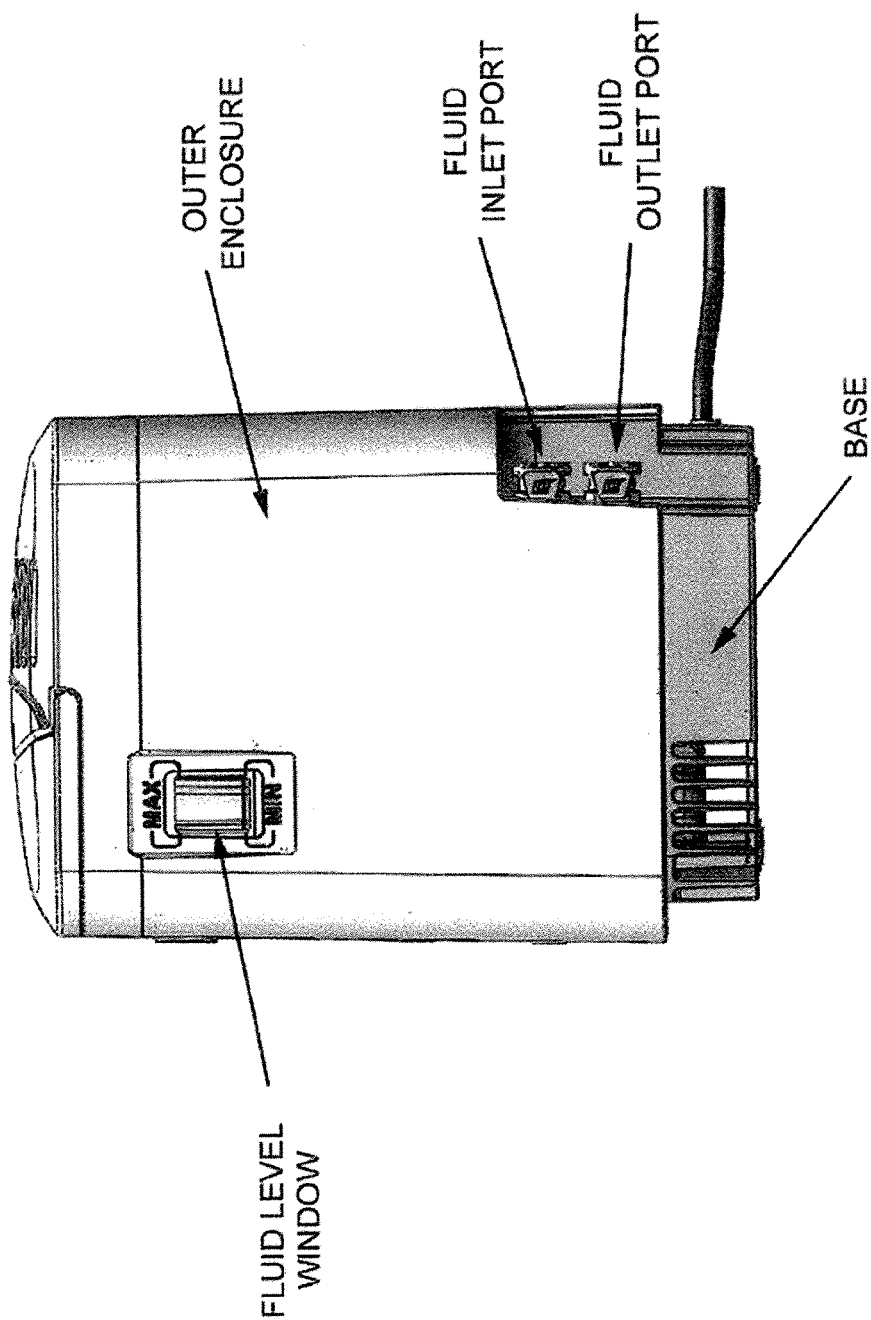
Figure 1C:
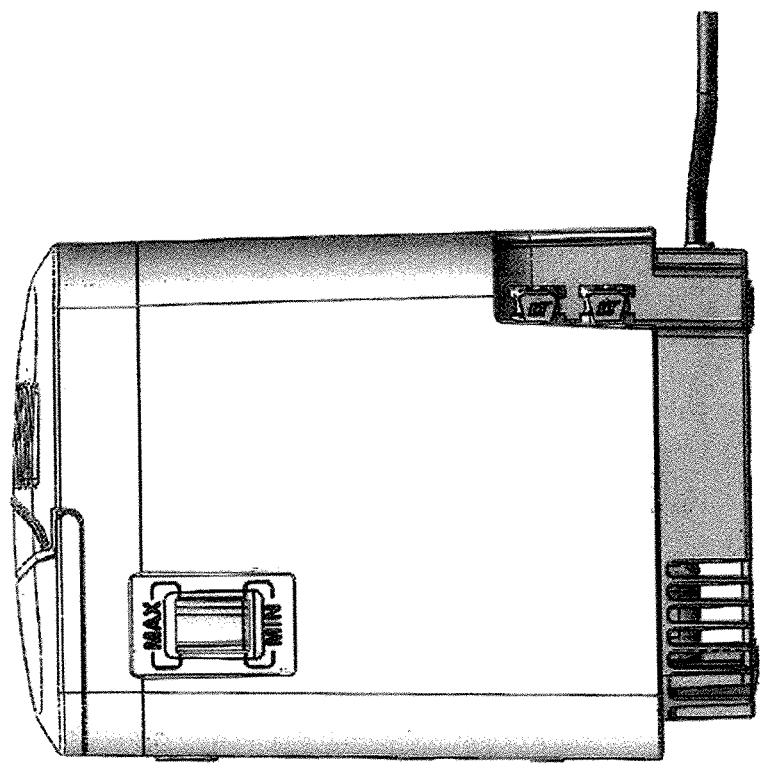
Figure 1D:
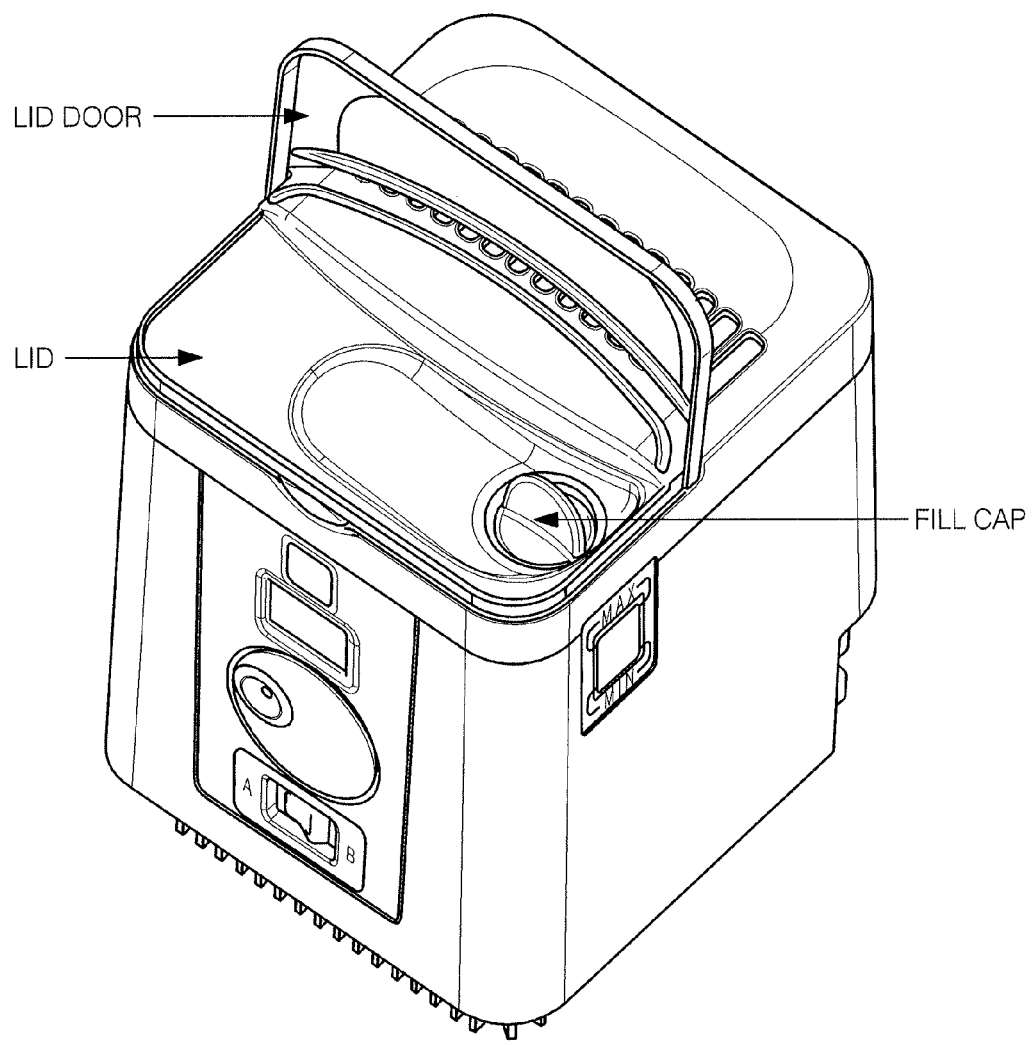
Figure 1E:
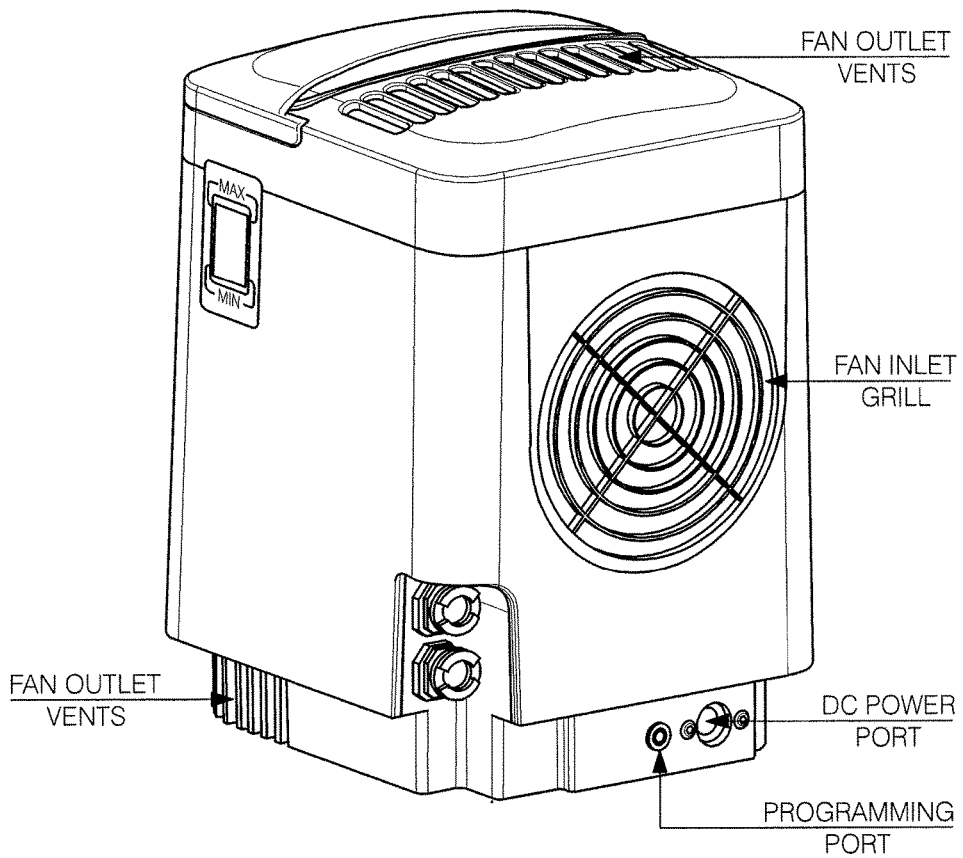
Figure 1F:
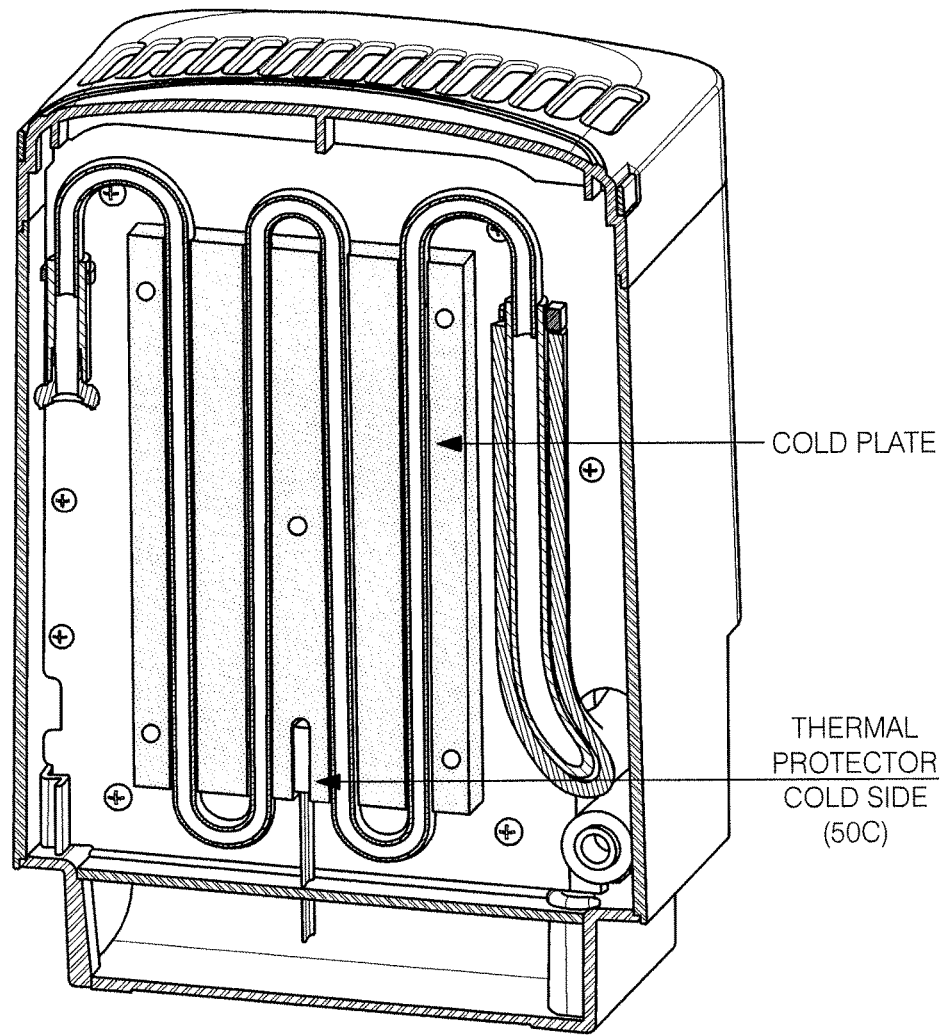
Figure 1G:
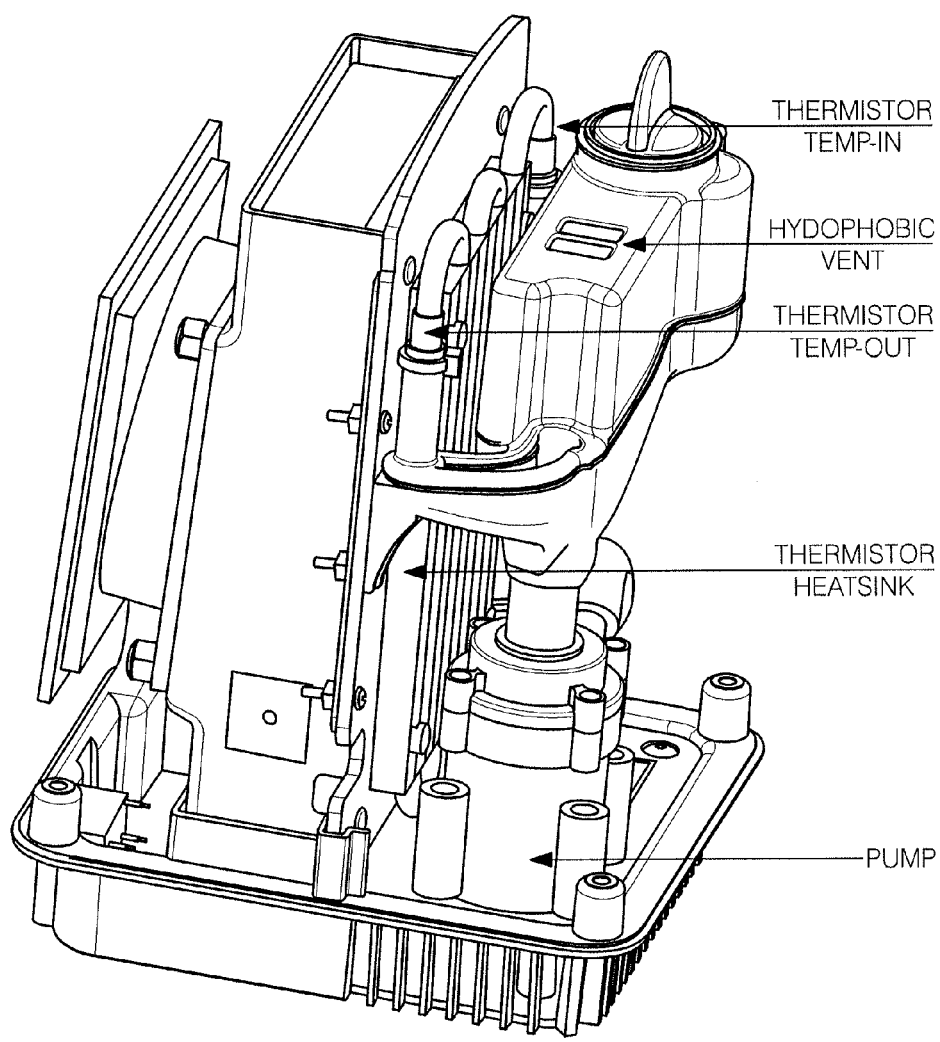
Figure 1H:
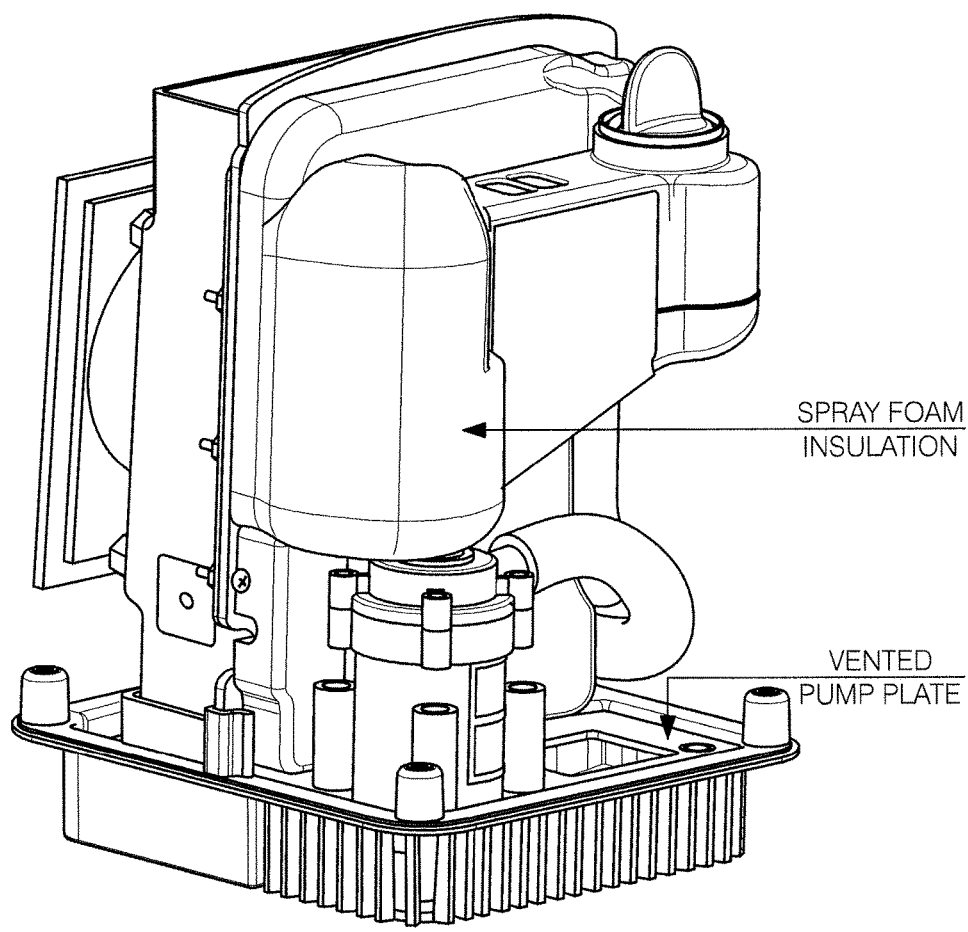
Figure 1I:
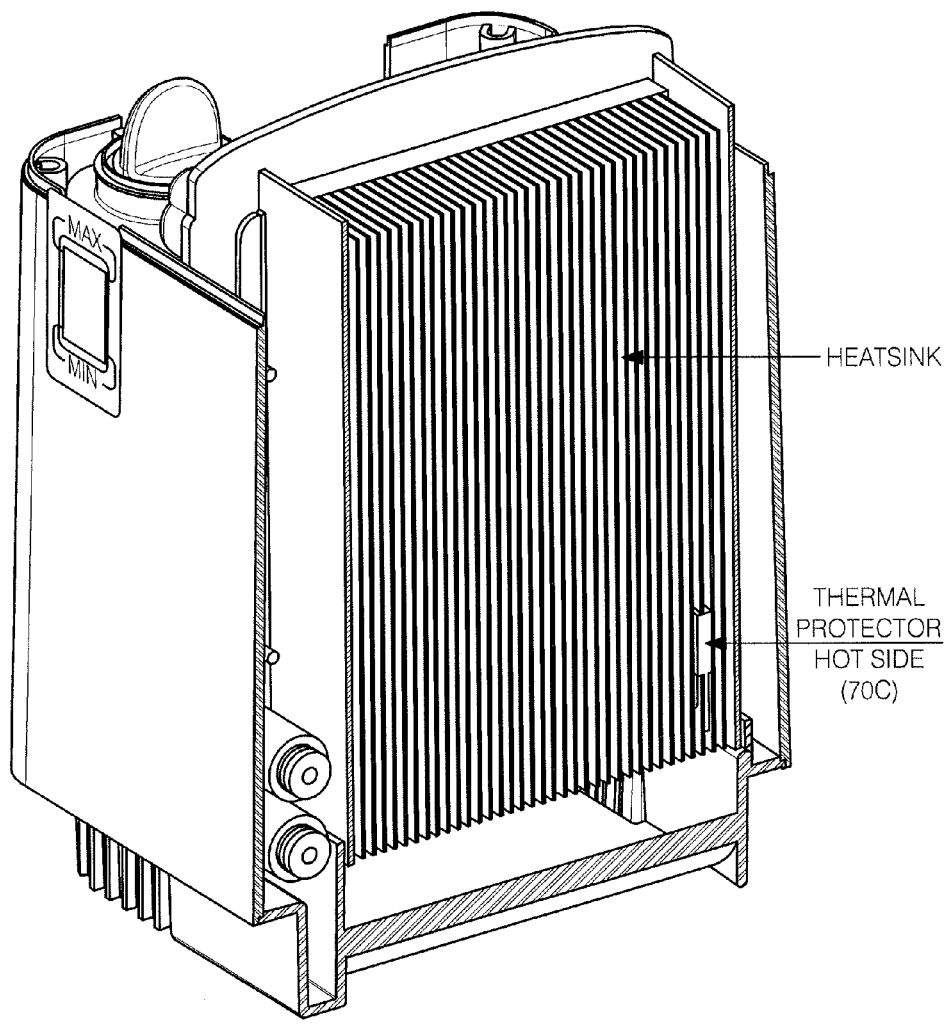
Figure 1J:
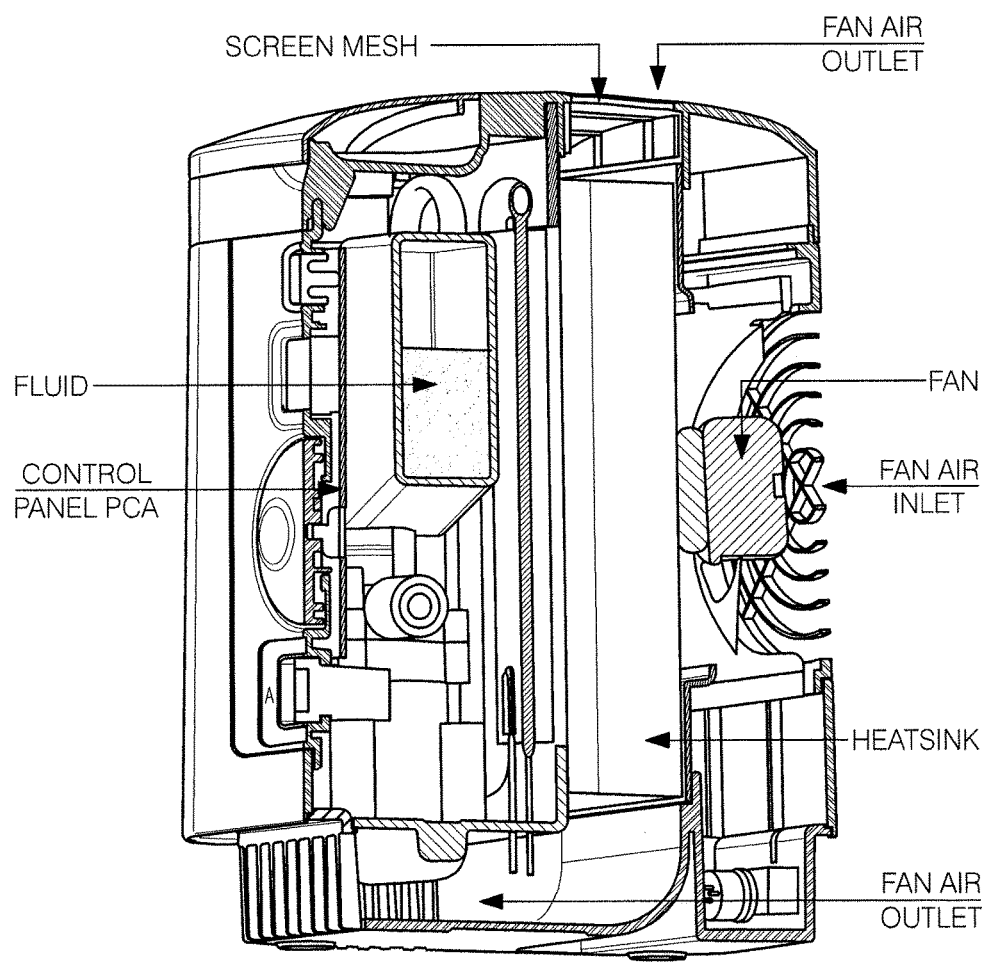

Described herein are apparatuses (including devices and systems) that specifically control the temperature of a patient's forehead region to modulate sleep. For example, described herein are apparatuses and methods configured to provide a temperature at the patient's forehead that is greater than ambient temperature (e.g., in some variations between about 25° C. and about 42° C.) for a period of time, which may be a predetermined period of time, to reduce sleep latency, enhance depth of sleep, and/or extend the time a subject sleeps. In some variations the subject may be a subject suffering from insomnia.

As used herein the term "warm" or "warming" generally refers to the temperature relative to the ambient temperature surrounding a subject, such as the ambient air temperature (e.g., typically 22° C.) surrounding the subject. A subject wearing an apparatus may perceive a stimulus greater than ambient temperature as "warm", even if the actual temperature of the thermal transfer region of the applicator is lower than the skin surface temperature. Thus, the thermal stimulus applied may be referred to as "warm" or "warming" based on the perception of the thermal transfer region when applied to the subject's forehead, likely because of activation of thermoreceptors in the subject's skin. Thus, in some instances it may be more accurate to refer to warming relative to subject perception (e.g., relative to the ambient temperature). In general, the warm or warming temperature may be between about 25 and 42° C. (e.g., between 25-40° C.).

The restorative nature of sleep and studies demonstrating abnormal hyperarousal in insomnia patients described in the medical literature suggests that the restorative aspects of sleep can be linked regionally with heteromodal association cortex, especially in the frontal regions. Two studies were performed to clarify the regional cerebral metabolic correlates of this. In the first study, changes in regional cerebral metabolism that occur between waking and sleep in healthy subjects were identified. Fourteen healthy subjects (age range 21 to 49; 10 women and 4 men) underwent concurrent EEG sleep studies and [18F]fluoro-2-deoxy-D-glucose ([18F]-FDG) positron emission tomography (PET) scans during waking and NREM sleep. Whole brain glucose metabolism declined significantly from waking to NREM sleep. Relative decreases in regional metabolism from waking to NREM sleep were found in heteromodal frontal, parietal and temporal cortex, and in dorsomedial and anterior thalamus. These findings are consistent with a restorative role for NREM sleep largely in cortex that subserves essential executive function in waking conscious behavior. In the second study, changes in regional cerebral metabolism were identified that occur between usual NREM sleep and recovery NREM sleep following a night of sleep deprivation. In this study, homeostatic sleep need, or sleep drive, was modulated in a within-subjects design via sleep deprivation. Four young adult healthy male subjects (mean age+s.d.=24.9±1.2 years) received NREM sleep using [18F]fluoro-2-deoxy-D-glucose positron emission tomography ([18F]-FDG PET) assessments after a normal night of sleep and again after 36 hours of sleep deprivation. Both absolute and relative regional cerebral glucose metabolic data were obtained and analyzed. In relation to baseline NREM sleep, subjects' recovery NREM sleep was associated with 1) increased slow wave activity (an electrophysiological marker of sleep drive); 2) global reductions in whole brain metabolism; and 3) relative reductions in glucose metabolism in broad regions of frontal cortex, with some extension into parietal and temporal cortex. The results demonstrate that the homeostatic recovery function of sleep following sleep deprivation is associated with global reductions in whole brain metabolism as well as greater relative reductions in broad regions of largely frontal, and related parietal and temporal cortex. In other words, sleep deprivation accentuates the decrease in brain metabolism normally seen during NREM sleep. A medical device that alters metabolism in a pattern similar to that seen in healthy sleep or recovery sleep following sleep deprivation, therefore, could benefit insomnia patients.

A study of insomnia patients investigated how these normal changes in brain metabolism become disturbed in insomnia patients. Insomnia patients and healthy subjects completed regional cerebral glucose metabolic assessments during both waking and NREM sleep using [18F]fluoro-2-deoxy-D-glucose positron emission tomography (PET). Insomnia patients showed increased global cerebral glucose metabolism during sleep and wakefulness. A group x state interaction analysis confirmed that insomnia subjects showed a smaller decrease than did healthy subjects in relative metabolism from waking to NREM sleep in the ascending reticular activating system, hypothalamus, thalamus, insular cortex, amygdala and hippocampus and in the anterior cingulate and medial prefrontal cortices. While awake, in relation to healthy subjects, insomnia subjects showed relative hypometabolism in a broad region of the frontal cortex bilaterally, left hemispheric superior temporal, parietal and occipital cortices, the thalamus, hypothalamus and brainstem reticular formation. This study demonstrated that subjectively disturbed sleep in insomnia patients is associated with increased brain metabolism. Their inability to fall asleep may be related to a failure of arousal mechanisms to decline in activity from waking to sleep. Further, their daytime fatigue may reflect decreased activity in prefrontal cortex that results from inefficient sleep. These findings suggest interacting neural networks in the neurobiology of insomnia. These include a general arousal system (ascending reticular formation and hypothalamus), an emotion regulating system (hippocampus, amygdala and anterior cingulate cortex), and a cognitive system (prefrontal cortex). Notably, ascending arousal networks are functionally connected to cortical regions involved in cognitive arousal at the cortical level which can feedback and modulate more primitive brainstem and hypothalamic arousal centers. A medical device that alters metabolism in one or more portions of this network could benefit insomnia patients and produce more restful sleep.

A second study in insomnia patients was conducted to clarify the cerebral metabolic correlates of wakefulness after sleep onset (WASO) in primary insomnia patients testing the hypothesis that insomnia subjects with more WASO would demonstrate increased relative metabolism especially in the prefrontal cortex given the role of this region of the brain in restorative sleep and in cognitive arousal. Fifteen patients who met DSM-IV criteria for primary insomnia completed 1-week sleep diary (subjective) and polysomnographic (objective) assessments of WASO and regional cerebral glucose metabolic assessments during NREM sleep using [18F] fluoro-2-deoxy-D-glucose positron emission tomography (PET). Both subjective and objective WASO positively correlated with NREM sleep-related cerebral glucose metabolism in the pontine tegmentum and in thalamocortical networks in a frontal, anterior temporal, and anterior cingulate distribution. These effects may result from increased activity in arousal systems during sleep and/or to activity in higher order cognitive processes related to goal-directed behavior, conflict monitoring, emotional awareness, anxiety and fear. These processes are thought to be regulated by activity of the prefrontal cortex.

As described herein, forehead warming may provide an indirect path towards activating warm sensitive neurons in the hypothalamus that are sleep promoting. Based primarily on the experimental data discussed below, and shown in the figures, experimental observations suggest that a medical device that produced regional warming to the forehead (e.g., scalp) may improve sleep in insomnia patients, allowing them to transition to sleep more easily and to subsequently obtain more restful sleep across the night. The subsequent increase in slow wave sleep may be expected to lead to reductions in metabolic activity in frontal cortex demonstrated in insomnia patients.

Figure 2A:
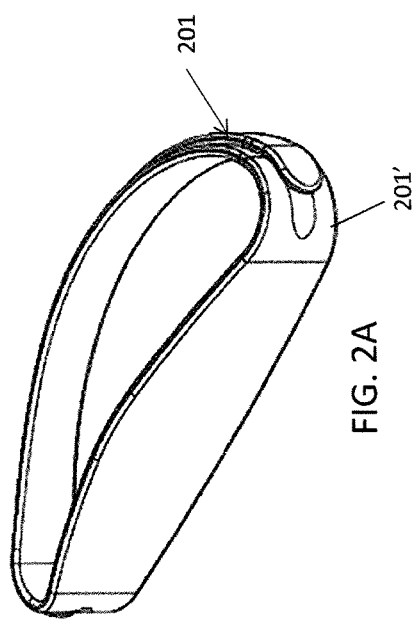
FIG. 2A shows one variation of an applicator portion of an apparatus for enhancing sleep by increasing forehead temperature relative to ambient temperature.

Apparatus for Enhancing Sleep by Increasing Forehead Temperature Relative to Ambient Temperature In general, any of the apparatuses for enhancing sleep by warming forehead temperature (relative to ambient temperature) described herein may include an applicator (e.g., pad, etc.) that fits against a subject's forehead and can be worn before and/or during sleep. FIG. 2A shows one variation of an applicator. In this example, the applicator includes a skin-contacting surface to be worn against the forehead (not visible) and a pair of side straps 201, 201' (securements) that can be adjusted so that the apparatus fits the subject. The applicator either connects to or includes a thermal regulator that controls the temperature at the skin-contacting surface of the applicator. The thermal regulator may also include timing controls to regulate the duration of applied temperature. The applicator may be secured in place by an included securement (e.g., strap, adhesive, cap, etc.). A control or controls for setting parameters controlled by the thermal regulator may also be included; in general, the controls may allow a user or bedmate to select parameters or modes of operation, as described herein. In some variations the system may include a disposable component and/or reusable components. For example, the skin-contacting surface of the applicator may be disposable and may be attached to the rest of (a reusable component) the applicator.

For example, in some variations, an apparatus for enhancing sleep by warming the forehead relative to the ambient temperature may include a custom-sized headpiece to fit the area of the scalp over the frontal cortex that circulated varying temperature fluids and a programmable warming chamber/pump that provided the warming and power for circulating the fluid to the headpiece.

In one example of an apparatus for enhancing sleep by increasing forehead temperature relative to the ambient temperature, the apparatus includes a thermal regulator unit, a thermal applicator/hose assembly (sometimes referred to as the forehead pad) and a headgear to maintain the thermal applicator in contact and in position with the frontal cortex. As mentioned above, the apparatus described herein may be worn by a sleeping subject, and thus may be adapted for comfort as well as safety and efficacy. In variations including a fluid (including a circulating fluid), the apparatus may be configured to prevent fluid loss/leakage. An apparatus for enhancing sleep by increasing forehead temperature relative to the ambient temperature may also be used without a circulating fluid. For example, by directly heating (including resistive heating) of the skin-contacting surface of the applicator. An apparatus for enhancing sleep by decreasing (or increasing) forehead temperature relative to the ambient temperature may also be used without a circulating fluid. For example, by directly cooling (including thermoelectric cooler, convection coolers such as fans, etc.) of the skin-contacting surface of the applicator.

For example, a thermal regulator unit may utilizes thermal electric modules (TECs), to heat (or cool) the applicator directly, or to heat a thermal transfer fluid (TTF) which is pumped through transfer lines of the thermal applicator. Other heaters such as resistive heating coils, chemical heating (e.g., exothermic reactions), high specific-heat capacity materials, or phase-change materials could also be used as part of the thermal regulator unit; other coolers (including chemical coolers) may be used.

Figure 2B:
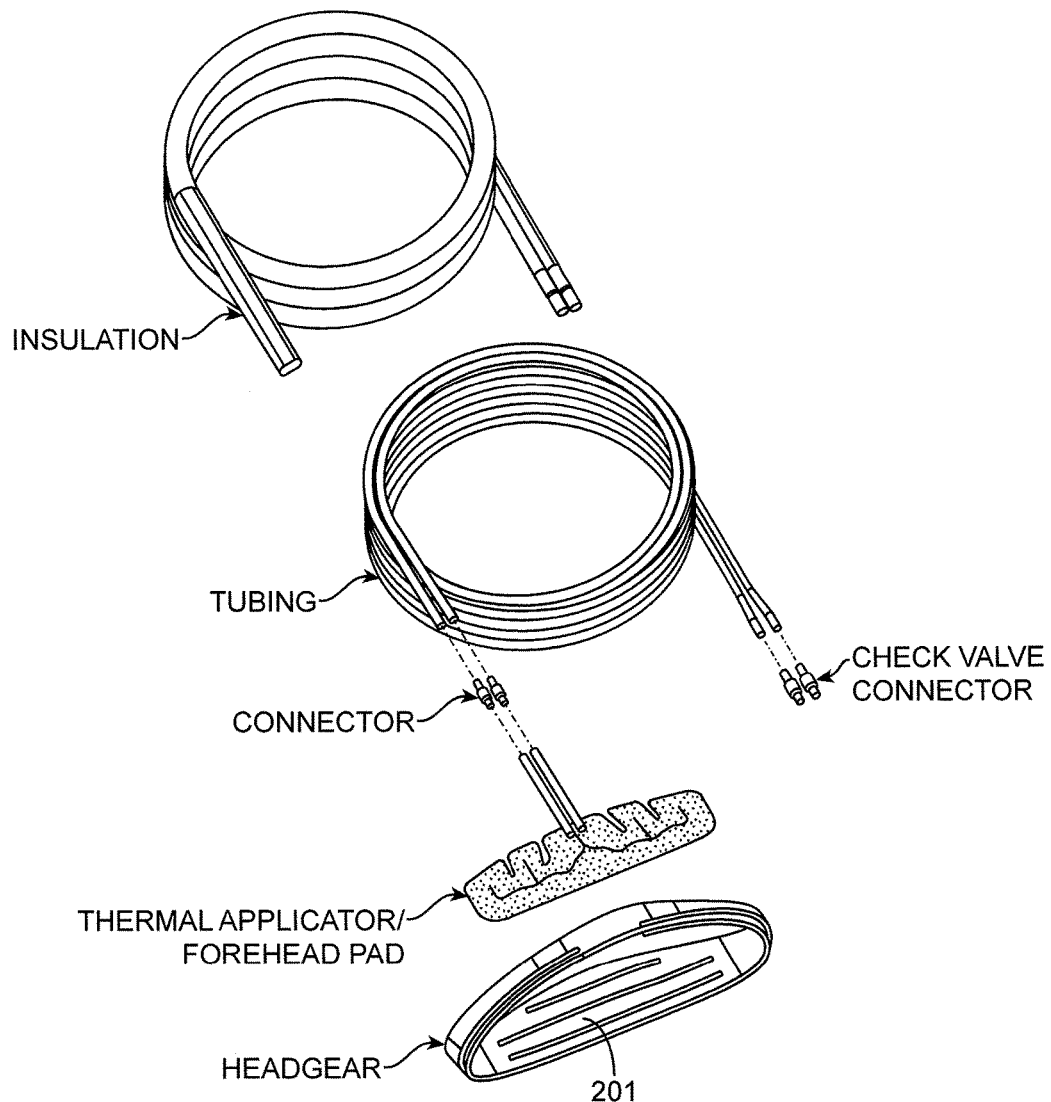
FIG. 2B illustrates one variation of an applicator for an apparatus for enhancing sleep by increasing forehead temperature relative to ambient temperature. This applicator may be used in conjunction with the apparatus of FIGS. 1A-1G.

In one variation, the apparatus is configured to operate with a TFF (fluid) to heat the applicator. Major components of such a thermal regulator unit may include a one or more heat exchangers, heat sinks, TECs, a pump, fan, electronic control circuits, software, user interface, TTF reservoir, unit enclosure, connections for incoming electrical power, and TTF connections for the thermal applicator. FIG. 2B shows a variation of an applicator for use with a TFF base unit including tubing 4 covered by insulation 5 that connects the thermal transfer region 2 of the applicator that also includes a headgear 1 having a skin-contacting surface 201.

In some variations, the components may be assembled such that the heat sink(s) are placed in thermal contact with one side of the TEC(s) and the heat exchanger is placed in thermal contact with the opposite side of the TEC(s) away from the heat sink. The heat exchanger can be constructed from any known material and design for the purpose. Portions of the assembly can be insulated to reduce parasitic heat loads on the heat exchanger. The thermal regulator unit can be operated in a warming (or cooling) mode to control the temperature of the TTF to the desired levels. The thermal regulator utilizes a pump to circulate the TTF through the heat exchanger and the thermal applicator. The pump can be of any appropriate type, i.e. centrifugal, piston, gear, diaphragm etc. A TTF reservoir is incorporated to provide additional TTF to replenish the TTF lost for any reason. The reservoir can be an integral fellable component within the thermal regulator unit or can be constructed as a replaceable cartridge. The plumbing connection for the reservoir may be designed such that the volume of the TTF within the reservoir is not serially located within the TTF circulation circuit of the heat exchanger and the thermal applicator. This design is referred to as a side stream reservoir. FIGS. 1A-1J illustrate one variation of a thermal regulator device for use with a TTF as described herein.

The side stream configuration effectively allows the thermal regulator to heat/cool the circulating TTF to the desired temperature faster by eliminating the need to heat/cool the TTF held in the reservoir. The reservoir or replaceable cartridge can be sized as required to provide the desired capacity for the user's convenience. The replaceable cartridge can be configured with a valve system that allows the user to engage or remove the cartridge into the thermal regulator without causing a leak of TTF. The cartridge may be configured with a one way vent to allow air intake as the TTF is drained from the cartridge. This configuration allows the TTF to drain from the cartridge and not re-enter the cartridge if a back pressure is generated within the circulating circuit. If this type of one way vent is utilized in the cartridge, a separate air vent may be plumbed into the circulation circuit to allow air trapped within the circuit to exit. Another configuration of the cartridge utilizes two connection points into the thermal regulator. One connection allows air trapped within the circulation circuit to vent into the cartridge while TTF is allowed to drain into the circulation circuit from the second connection point. The connection valves may be designed in any number of known configurations. One such implementation utilizes check valves in each of the mating connection components. This may provide a means of engaging or removing the cartridge without TTF leaking from the removed cartridge or from the mating connection point within the thermal regulator. In another variation the cartridge is sealed with a rubber type material that can be punctured with a hollow needle. Once punctured the TTF would make a fluid connection with the circulation circuit. When the cartridge is removed, the needle would be withdrawn allowing the rubber type material to reseal the puncture hole preventing the TTF from leaking from the cartridge. The needle would be designed with a spring loaded sliding rubber type material seal that would slide over the inlet port on of the needle when the cartridge is removed. Another variation utilizes ball type or O-ring seal type check valves commonly known. The cartridge size and shape are determined by the required capacity, the desired cosmetic industrial design and the available space within the enclosure. Once engaged in the thermal regulator, the cartridge is held in place by any latching mechanism. In another embodiment, the cartridge air vent is bi-directional and may be constructed of a material such as Gore-Tex. Such a material allows air to pass through it while preventing TTF from passing.

In some variations the cartridge may include a liner holding the fluid within the cartridge, and the liner may be collapsible as fluid is removed and expandable as fluid is added to the cartridge. In variations including a collapsible liner (bag or holder), the cartridge may not need or include a vent into the fluid, and the fluid reservoir held by the liner may be isolated from the environment, reducing the likelihood of leakage.

The cartridge and engagement valves are designed to prevent or minimize the potential of the user refilling the cartridge. This design will ensure the user only utilizes TTF specifically formulated for the cooling unit.

The TTF can consist of but is not limited to distilled water, an anti-microbial agent, a component to lower the freezing point and a wetting agent. Other TTF ingredients could also be used. All TTF may be compliant with the bio compatibility requirements of IEC 60601 and FDA requirements.

The control circuits may or may not utilize software for controlling the cooling or heating of the thermal regulator unit. The control circuit may utilizes one or more thermistors located within or in proximity to the circulating circuit to measure the temperature of the TTF and adjust the power to the TECs as required to maintain the TTF within the circulating circuit at the desired temperature. Additionally, the control circuit can utilize one or more thermal control switches located on the heat sink and possibly the heat exchanger as a safety switch in case temperatures on one or both components are outside the desired thresholds. The control circuit may utilize Pulse width modulation (PWM) to provide power to the TECs, pump and fan. Software can also be utilized to provide control algorithms for controlling all aspects of the system. The software could control the power to be supplied to the TECs in such way to produce any desired cooling curve of the TTF. In one variation the power could be applied to the TECs such that the TTF is cooled more rapidly with the onset of power and the rate of temperature change is reduced as the actual TTF temperature and targeted TTF temperature difference becomes smaller. There are other temperature curves that could be considered. Additionally, the TTF temperature could be controlled by user physiological measurements or by time. The control circuits can also provide a user interface to the cooling unit. Possible variations could include but not be limited to an on/off switch, heat/cool mode selector switch, temperature display of targeted temperature or actual temperature of the TTF. The control circuit could also control display lighting. In some variations the control circuit can monitor the level of TTF in the reservoir or cartridge and display the level to the user. The control circuit could also shut the unit off if it detected a low or empty TTF level.

The enclosure provides a means of mounting all of the internal components of the system and provides for air intake and exhaust of the fan air. The fan inlet and exhaust can be directed through a grid system within the enclosure that is designed to prevent users from coming in contact with components that could produce an injury. Furthermore, the grids may be designed in such a way to allow the user to direct the airflow in a direction they find desirable. The enclosure allows for a conveniently positioned user interface, reservoir filling or cartridge replacement, a visual means for determining the TTF level remaining, connection points for incoming power, connection points for the inlet and outlet of the circulating circuit thermal applicator/hose assembly and any other desirable connections.

The inlet/outlet connectors of the thermal applicator/hose assembly and the thermal regulator enclosure connectors utilize check valves that allow the thermal applicator/hose assembly to be connected and removed from the regulator assembly without leaking TTF from either component. The hose portion of the assembly is sufficiently insulated to prevent or minimize condensation on the hose assembly to the desired ambient temperature and humidity conditions. The thermal applicator component of the system may be designed to form a seal between at least two layers of flexible rubber like material. The seal may be formed by any known technique such at ultra-sonic welding, RF welding, adhesive bonding or chemical welding. The flexible material layers are selected from a wide range of known materials that exhibit the desired material properties such as flexibility, conformability, permeability, comfortable feel for the user etc. such as urethane or vinyl sheet. It is desirable the material is bio-compatible. The seal formed between the layers forms a flow channel or passageway for the TTF to circulate while the applicator is in contact with the user's skin. The thermal applicator acts as a heat exchanger when used in this way. The TTF which is temperature controlled by the thermal regulator is pumped through the hose portion of the assembly into the thermal applicator in contact with the user's skin. Thermal energy is transferred to or from the user depending upon the selected temperature of the TTF and the user's skin temperature. The design of the channels and the total length of channels produced by forming the seal between the layers of the applicator effect the amount of energy transferred. The design of the channels and the circulation path within the applicator also effect the temperature variation within the applicator. It is desirable to design the channels in such a way to maintain an even distribution of temperature across the applicator. The inlet and outlet connections of the hose to the thermal applicator may be made permanent or utilize the type of connections that can be disconnected. The design of the channels within the applicator may vary in size or cross sectional area to produce desired pressures, temperatures or flows within the channels. Additionally, the use of small weld spots or dots within the flow channels may be used to control ballooning of the channel while under pressure. The outer perimeter of the applicator is designed to provide contouring of the applicator to the desired portion of the user's skull in proximity to the fontal/prefrontal cortex. This area is generally defined as the area including the left and right temple area and the area defined between the eyebrows and the top center of the head. The applicator perimeter may also include a variety of cuts, slits or other geometrical definitions that allow the applicator to better contour to the user's head within the desired contact area. FIG. 2B shows one variation of the applicator and depicts the aspects of the design discussed.

Figure 3:
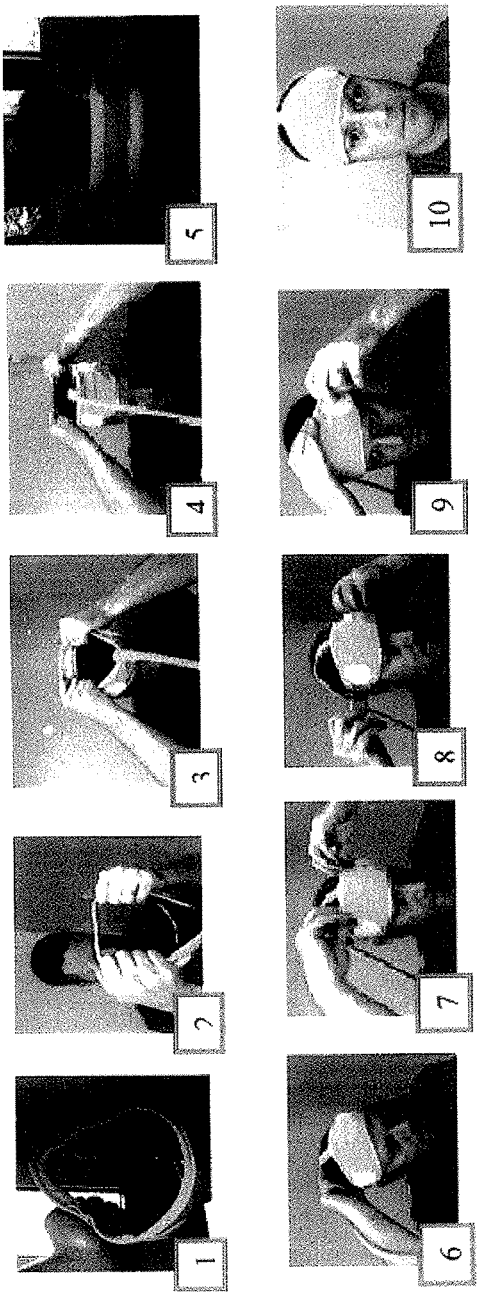
FIG. 3 illustrates one variation of a method of applying an applicator of an apparatus for enhancing sleep by increasing forehead temperature relative to ambient temperature.

The thermal applicator may be held in contact with the subjects head with a head gear system, as illustrated in FIG. 3. In one variation of the headgear component, a series of adjustable straps are used to selectively adjust the contact pressure of the applicator to the user. Other variations of the headgear can be constructed with and elastic type material without adjustability. The elastic nature of the material applies contact pressure to the thermal applicator. Other variations utilize both features, i.e. adjustable straps and elastic materials. In some variations the thermal applicator can be permanently integrated with the headgear and in other variations, the thermal applicator can be removable from the headgear.

As mentioned, the applicator portion of the apparatus generally includes as skin-contacting region configured to lie against the subject's forehead. The skin-contacting region generally includes the thermal transfer region. Temperature is only regulated actively over the thermal transfer region, which is preferably the region of the subject's forehead. The applicator may be configured so that other regions of the subject's head or face are not in contact with the thermal transfer region; thus temperature regulation may only be applied to the forehead but not to other regions such as the eye orbits, cheeks, neck, back of the head, hairline, etc. Thus, in some variations the applicator may contact or cover other regions, not just the forehead, but the thermal transfer regions may only contact the forehead but not the eye (periorbital and orbial regions) or cheek regions.

The applicator may generally be configured to enhance wearer comfort. For example, the applicator may have a relatively thin thickness (e.g., less than 5 cm, less than 2 cm, less than 1 cm, etc.), so that it can be comfortably worn while sleeping. The applicator may adjustably fit to a variety of patient head circumferences.

In general any of the apparatuses described herein may be configured to apply a temperature that is greater than the ambient temperature surrounding the subject. In some variations this means controlling the patient-contacting (skin-contacting) surface of the applicator to a temperature that is between 25° C. and 40° C. (e.g., 27° C., 28° C., 29° C., 30° C., 31° C., 32° C., 33° C., 34° C., 35° C., 36° C., 37° C., 38° C., 39° C., 40° C., or any intermediate temperature there between). The temperature may be held constant or varied (or allowed to vary) within a range (e.g., between about 27° C. and 40° C., etc.).

In some variations the temperature applied may be determined based on the relative ambient temperature. For example, the temperature applied may set to a predetermined amount ($\Delta_{Temp}$) warmer than the ambient temperature (e.g., 0.5° C. warmer than ambient, 1° C. warmer than ambient, 1.5° C. warmer than ambient, 2° C. warmer than ambient, etc.). In some variations, the maximum temperature may be limited to 40° C.

Method of Operating the Apparatus and Experimental Results

FIG. 3 illustrates one method of applying an applicator to a subject's head. The applicator may be readily applied by the subject to his/her own head. The applicator may generally be applied immediately or shortly before going to bed. FIG. 3(1) shows one example of an applicator. The subject (which may also refer to the patient) may then apply he device against their forehead, as shown in FIGS. 3(2)-3(5), and adjust the straps (e.g., the securements) on the device so that the device is comfortable and secure, as shown in FIGS. 3(6)-3(9). In this example, the applicator includes a TFF and thus a tube runs from the applicator to the base unit not shown in FIG. 3A, but see FIGS. 1A-1J. This variation of an applicator may include a tube or tubes extending from the device to the base unit, and the tubes may be adjusted along with the applicator over the subject's head. Once in place, the subject may then go to bed.

A study using a device similar to that shown in FIGS. 1A-1J and 2B was used to improved sleep in insomnia patients. The primary aim of this study was to compare EEG sleep outcome measures, tolerability and safety in 150 evaluable primary insomnia patients using the apparatus at 2 temperatures, 30° C. and 14° C. For simplicity sake, the 14° C. temperature may be referred to as a "cooling" or "cool" temperature, and the 30° C. temperature may be referred to a "warming" or "warm" temperature, even if the patient's skin surface is warmer than 30° C.

Figure 4:
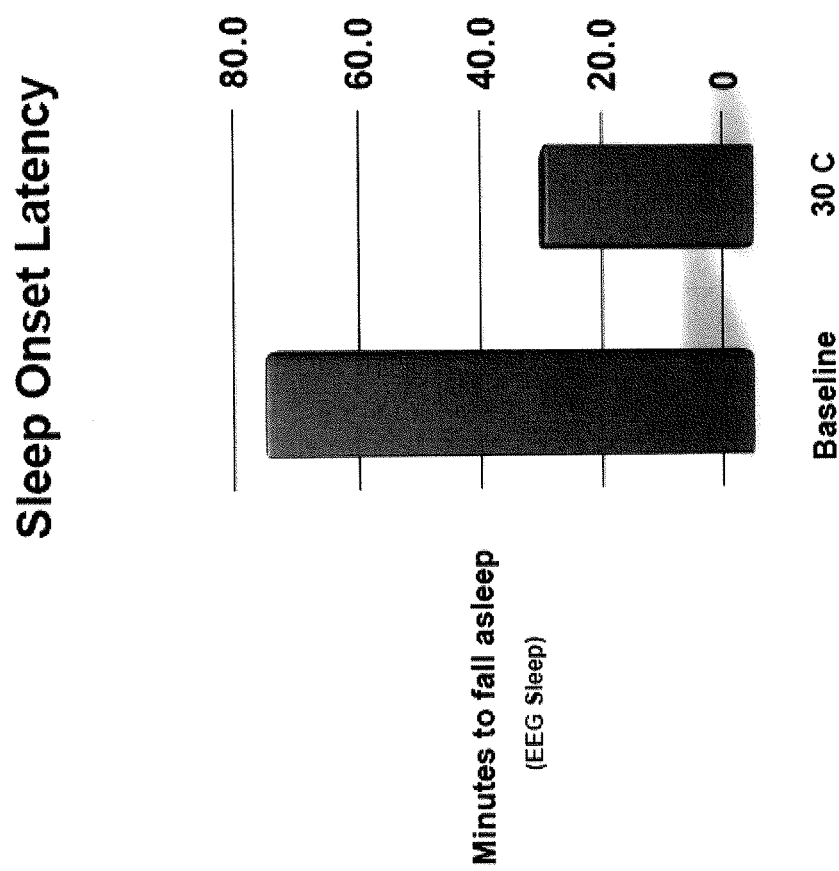
FIGS. 4-13B illustrate the results of a study examining the effects of the operation of a device such as those shown in FIGS. 1-3B on a population of subjects.

Based on the data collected by this experiment, the latency to persistent sleep based on sleep electroencephalogram (EEG) obtained during the polysomnogram showed that the sleep efficiency based on sleep EEG obtained during the polysomnogram during heating was significantly improved relative to the baseline. This is shown in FIG. 4. Baseline refers to the untreated subject, not controlling the temperature of the forehead.

The apparatus used for the investigation included three components: (1) a temperature controlling unit which provides the means to regulate the temperature of the fluid and transport the fluid from the unit to the forehead pad; (2) a forehead pad; and (3) a headgear. The temperature controlling unit utilizes solid state thermoelectric devices to regulate the temperature of a thermal transfer fluid consisting of distilled water and alcohol. The temperature controlling unit has a user interface that allows the user (clinician) to turn the unit on and off, adjust the temperature and select between the 30° C. and 14° C. mode. The unit contains a pump for circulating the thermal transfer fluid through the tubing and forehead pad. The forehead pad provides the actual temperature regulation to the subject, by including a skin (patient) contacting surface having a thermal regulation region. The forehead pad was fabricated from a urethane film sheet that is used in other common medical products. The headgear provided a mechanism to hold the forehead pad in place. The headgear is fabricated from a clothing grade lycra based material.

The study was a multi-center prospective, blinded, randomized crossover study to compare the device at two different temperatures in primary insomnia patients. Potential subjects were required to undergo screening using a variety of methods. Phone screening was used to initially screen out those who would not meet inclusion/exclusion criteria. Potential subjects who agreed to continue with the screening process were sent a short Informed Consent document to complete, providing written agreement to continue with screening activities and allow provision of study-related materials to be sent to their home address. Following receipt of the signed screening consent form, potential subjects completed a one week sleep wake diary and study questionnaires. After completion of the diary, clinic visit one was scheduled. Informed consent will be obtained at clinic visit one for the remainder of the study. Clinic visit one was used to determine initial eligibility into the trial. Upon determining initial eligibility, the first PSG was scheduled to rule out ancillary sleep disorders. If negative for sleep disorders and the criteria for sleep latency and efficiency were met, a second night of baseline/screening PSG was conducted. Data from these two studies provided a basis for inclusion into the study. If deemed eligible, subjects were randomized to start with either one or the other temperature condition.

Once randomized, each subject had two sequential nights in each condition. Subjects had a total time in bed of 8 hours and were expected to wear the device for the entire time in bed. Each dyad of nights was separated by 3-5 nights non-intervention sleep at home. The forehead pad and headpiece was placed on the subjects head at 30° C. Five minutes after the application of the headgear and forehead pad to the subject, the condition was set according to the randomization scheme (A or B). There was a 25 minute time delay between when the device was set and achieving 15° C. After 25 minutes of acclimation time, patients in both groups will be informed that they are able to maximally adjust the temperature+/−1° C. according to comfort. In the 30° C. setting, the temperature adjustment function was disabled and the temperature remained at 30° C. Once the comfort setting was chosen, no further adjustments were allowed for the remainder of the night.

A Central Scoring Service (CCS) provided overall PSG study guidance to the sites. In addition, they provided the centralized scoring of the PSG data. All sites followed a standard sleep protocol that included patient preparation procedures, standard recording montage, proper instrument calibration and bio-calibration procedures that must have preceded the initiation of the collection of the PSGs. A standardized set of instructions regarding how to monitor the PSGs including when to appropriately re-attach recording electrodes and how to record during patient middle-of-the-night bathroom breaks was provided.

According to the American Academy of Sleep Medicine (AASM) Manual for Scoring Sleep and Associated Events (2007), a standard PSG montage, recording channel labels and the order to be used was: left electrooculogram (E1/M2); right electrooculogram (E2/M1); submental electromyogram (chin1/chin2); submental electromyogram (chin2/chin3); electroencephalogram (C3/M2); electroencephalogram (O2/M1); electroencephalogram (F4/M1); electroencephalogram (C4/M1); and electrocardiogram (ECG). In addition, for the sleep disorder screening night (SN1), the following was added: thoracic inductance plethysmography (TEFFORT); abdominal inductance plethysmography (AEFFORT); nasal/oral thermal sensor (TFLOW); nasal/oral nasal air pressure transducer (PFLOW); oxygen saturation (SaO2); left anterior tibialis electromyogram (L LEG); and right anterior tibialis electromyogram (R LEG). The PSG was transferred to EDF format by the recording site and sent to the CSS for the scoring of sleep stages and sleep-related events. Sleep was scored in 30 sec epochs for standard sleep stages according to AASM criteria. Respiratory (SBD) and periodic leg movement (PLMS) events were scored according to the AASM criteria. The total number of sleep related breathing (SBD) events, apneas and hypopneas, were indexed to the hours of total sleep time as were the total number of PLMS (# events/hrs sleep).

Sleep Latency was calculated by polysomnographically derived primary endpoints from lights out to the first 10 min of continuous sleep, persistent sleep latency. The sleep efficiency was determined as TST/total recording time. All other EEG sleep measures were collected as standard measures of sleep including WASO (wake minutes after sleep onset), number of awakenings (2 consecutive epochs scored wake), number of brief AASM-defined arousals (3-15 sec shifts in EEG frequency to alpha, theta or greater than 16 Hz), and the minutes and percentages of sleep stages 1,2, delta NREM sleep and REM sleep in relation to total sleep time.

The patient population for this study was screened. Following the initial phone screening, 150 primary insomnia subjects were randomized. Subjects were recruited by print and other media advertisements, self-referrals, patient database, and word of mouth at 9 clinical sleep research sites. All genders and ethnic backgrounds were considered for this study and the study was limited to adults ≥22. This study involved adult men and women of all races and ethnic groups; represented in the proportions present in the regional population. The study did not involve subjects younger than 22 years of age, because the clinical characteristics of primary insomnia are not well-defined in this group. The study did not include other special classes of subjects, such as fetuses, neonates, pregnant women, prisoners, institutionalized individuals, or others who may be considered vulnerable populations.

An initial telephone screening was conducted using a standard script. Subjects were asked to agree to continue with the phone screening and verbal consent was obtained. Subjects meeting the initial phone screening criteria were sent via United States Postal Service or email a short informed consent form to allow study personnel to send study related documents to their residence.

Upon the sites receiving the signed informed consent form the following documents were sent to the subject's home: Insomnia Severity Index (ISI); one week Pittsburgh sleep-wake diary (diary could be completed up to two weeks prior to clinic visit 1 and up to SN1); and a self-administered medical history form. Upon the subject's completion of the one week Pittsburgh sleep-wake diary, clinic staff scheduled for an in-clinic visit (Clinic visit 1), wherein research staff reviewed the sleep-wake diary and the ISI for completeness and initial inclusion criteria. Calculations for sleep efficiency from the sleep-wake diary were done. After confirming the required sleep efficiency (85% on 50% of the nights) subjects were consented for the rest of the study. At clinic visit one, in addition to the aforementioned document review, the following was done: History/Interview (M.I.N.I., SCIDSLD); Review of concomitant medications; Urine drug screen; and Urine pregnancy test if indicated.

Individuals with well-controlled health conditions that do not affect sleep or well-being (e.g., well-controlled thyroid disorders, asthma, or ulcer) were not excluded. At this in person interview, in order to evaluate these criteria, potential subjects completed a medical history form of common medical problems.

The following instruments were used to assess inclusion and exclusion of secondary insomnia and co-morbid psychiatric, neuropsychiatric and medical conditions in conjunction with medical expertise include the following: Mini International Neuropsychiatric Interview (M.I.N.I.); physician review of the self-reported medical history; Insomnia Severity Index (ISI); SCIDSLD; Concomitant Medications; MedTox EZ-Screen and Human Chorionic Gonadotropin (HCG), Qualitative, Urine. The M.I.N.I. is a structured diagnostic interview to assess for the presence of DSM-IV and ICD-10 psychiatric disorders. The physician review of the self-reported medical history and patient interview provides a review of current and past medical history as needed to determine eligibility criteria. The Insomnia Severity Index (ISI): The ISI is a subjective rating scale that gives a value for insomnia severity. The SCIDSLD was used to make a diagnosis of insomnia and to rule out the presence of other sleep disorders. Concomitant Medications were assessed for chronic use of medications for exclusion. The MedTox EZ-Screen: Urine Drug Screen was also used. The Human Chorionic Gonadotropin (HCG), Qualitative, Urine was used to test urine for pregnancy.

As mentioned, inclusion criteria included: Age ≥22; signed informed consent; diagnosis of insomnia that meets criteria for DSM IV diagnosis of primary insomnia and ICSD general insomnia criteria and RDC insomnia disorder criteria (criteria include: a complaint of difficulty falling asleep, staying asleep, awakening too early, or non-restorative sleep, adequate opportunity for sleep, evidence of daytime impairment, minimum duration criterion of at least >1 month, and sleep complaints to be present on most days); subjects remained alcohol-free and avoid drugs that could affect sleep during the study; >14 on the Insomnia Severity Index; and Sleep-Wake diaries demonstrate sleep efficiency <85% on at least 50% of nights.

Exclusion Criteria included: a neuropsychiatric disorders that may independently affect sleep, brain function or cognition, such as current major syndromal psychiatric disorders, including DSM-IV mood, anxiety, psychotic, and substance use disorders; specific exclusionary diagnoses include major depressive disorder, dysthymic disorder, bipolar disorder, panic disorder, obsessive compulsive disorder, generalized anxiety disorder, any psychotic disorder, and any current substance use disorder. Unstable medical conditions including severe cardiac, liver, kidney, endocrine (e.g. diabetes), hematologic (e.g. porphyria or any bleeding abnormalities), other impairing or unstable medical conditions or impending surgery, central nervous system disorders (e.g., head injury, seizure disorder, multiple sclerosis, tumor), active peptic ulcer disease, inflammatory bowel disease, and arthritis (if the arthritis impacts sleep); Raynaud's Disease; Irregular sleep schedules including shift workers; A latency to persistent sleep <15 on either the sleep disorder screening night or the baseline PSG sleep night; a sleep efficiency >85% on either the sleep disorder screening night or the baseline PSG sleep night; an AHI (apnea hypopnea index) >10 and/or a periodic limb movement arousal index (PLMAI) >15 from SN1; a Body Mass Index >34; use of medications known to affect sleep or wake function (e.g., hypnotics, benzodiazepines, antidepressants, anxiolytics, antipsychotics, antihistamines, decongestants, beta blockers, corticosteroids) (Beta blockers which do NOT cross the blood brain barrier are acceptable); consumption of more than one alcoholic drink per day, or more than 7 drinks per week prior to study entry; consumption of caffeinated beverages >4/day or the equivalent of more than 4 cups of coffee; and unable to read or understand English.

In addition, if the urine drug screen was negative and other I/E criteria were met, the first of two in laboratory screening nights were scheduled. These are screening PSG (SN1) Clinic Visit 2 and Screening/Baseline PSG (SN2).

Subjects were asked to report to the sleep laboratory about 2-3 hours prior to their scheduled good night time (GNT) for 2 consecutive nights on 3 separate occasions, each separated by at least 3-5 days. All subjects had a fixed time in bed for monitoring of 8 hours. The good night time was determined as 4 hours prior to the mid-point of their sleep diary times in bed at home averaged over the one week period of the sleep-wake diary completion. The good morning time was determined as 4 hours after the mid-point of their sleep diary times in bed at home.

The recording took place in a separate, comfortable, darkened, sound-attenuated room with regulated temperature (18-20° C.-65-68° F.) and normal humidity conditions. Each sleep facility was equipped with a standardized thermometer and recorded the room temperature for each subject for each night in the sleeping room. Subjects were asked regarding concomitant medications and completed an in-lab version of the Pittsburgh home sleep diary. Subjects were required to have a breath test for alcohol consumption; if positive, the subject was not able to continue in the study. Subjects were fitted with electrodes for monitoring sleep parameters. PSG SN1 subjects were screened for sleep apnea and periodic limb movement disorder. (Clinic Visit 2). Sleep Clinic "quick" scores for sleep latency, sleep efficiency, AHI and PLMAI were performed, and if the study meets the inclusion criteria, they were schedule for SN2. PSG SN2 subjects slept uninterrupted with no device to collect baseline EEG sleep measures (Clinic Visit 3). The sleep clinic personnel scored the SN2 for sleep latency and sleep efficiency.

At DN1, randomization occurred. Subjects were randomized to the sequence, or order, of the settings of the Cerêve Sleep System in the sleep lab, 30° C. first or 15° C. first. Subject randomization was stratified by Study Center to ensure a balance of the order of the settings across all Study Centers. Subjects were randomized when they arrive for the first device night (DN1) in the sleep lab. Third party blinding for the scoring of sleep laboratory data was used to aid in control of bias. Subjects were not informed as to which temperature was hypothesized to be a therapeutic temperature. All study staff coming in contact with subjects were blinded as to which was a therapeutic condition. Third party blinding for the scoring of sleep data was used to reduce study bias. To the degree possible, all relevant study staff were blinded to the hypotheses. The PSGs were each scored by a team of scorers with documented scoring reliability and who were blind to treatment assignment. Subjects were blinded to the hypotheses.

During device Nights 1-4, the conditions for sleep included recording in a separate, comfortable, darkened, sound-attenuated room with regulated temperature (68°-72 F) and normal humidity conditions. Each sleep facility was equipped with a standardized thermometer and recorded the room temperature for each subject for each night in the sleeping room. Subjects were randomized to order of conditions. Subjects were also asked about concomitant medications and completed an in-lab version of the Pittsburgh home sleep diary for device nights 1-4. Subjects were required to have a breath test for alcohol consumption; if positive, they were not able to continue in the study. Subjects were fitted with electrodes for monitoring sleep parameters. At 65 minutes prior to good night time the device was turned on to allow for the time required to achieve a temperature of 30° C. At 60 min prior to GNT, on device nights (DN1, DN2, DN3 and DN4), with the subject sitting in a comfortable chair, the technologist assisted and/or applied the headgear with attached forehead pad (previously described) at a temperature of 30° C.

As soon as the headgear was on, the subject had photographs taken of the following: front of face, side of face and the top and the back of the head. Sunglasses could be worn if the subject chose to retain anonymity. Immediately after the photographs were taken, the subject was asked to sit quietly in a comfortable chair in the lab bedroom and not to engage in potentially stimulating activities such as using a cell phone or computer or watching television. The subject had limited contact of study staff during this time. After 25 minutes, the technologist offered the opportunity to make a one-time change +/−1° C. After making any settings change, the subject continued to sit for an additional 25 minutes. GNT: After 25 minutes has passed, the subject could lie down to begin their sleep period. The sleep period was defined as lights out to lights on. The subject had the device on their head for a total 60 minutes prior to GNT. Subjects stayed in bed for a total of 8 hours. Subjects were asked to keep the headgear and forehead pad on for the 8 hour time in bed period.

In the morning after device nights, the subject completed the morning questionnaire upon first waking. After the 8 hour in bed time the headgear was removed and the subject completed the morning questionnaire. The MMSE and adverse events assessments began 1 hour after awakening. A mini mental status exam (MMSE) was administered to subjects on the morning of the second night only in any given condition.

The results of the trail are illustrated in FIGS. 4 though 13B. As mentioned above, the study found that the sleep onset latency, as shown in FIG. 4, was substantially decreased over baseline. Thus in subjects whose forehead was contacted by an applicator having a thermal transfer region at 30° C., the average time to sleep was shortened from about 75 minutes to about 30 minutes (in an n of about 100 patients). The onset of sleep latency was determined by examining the patient ECG recordings as mentioned above, providing an objective measure of sleep onset. The data was highly significant (p values of <0.001).

Figure 5:
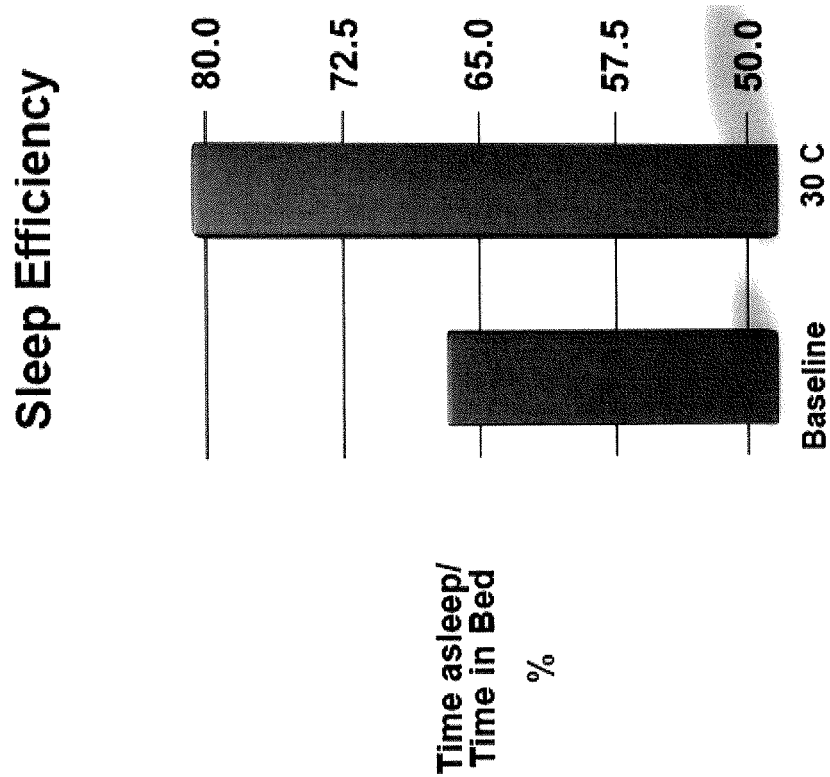
Figure 6:
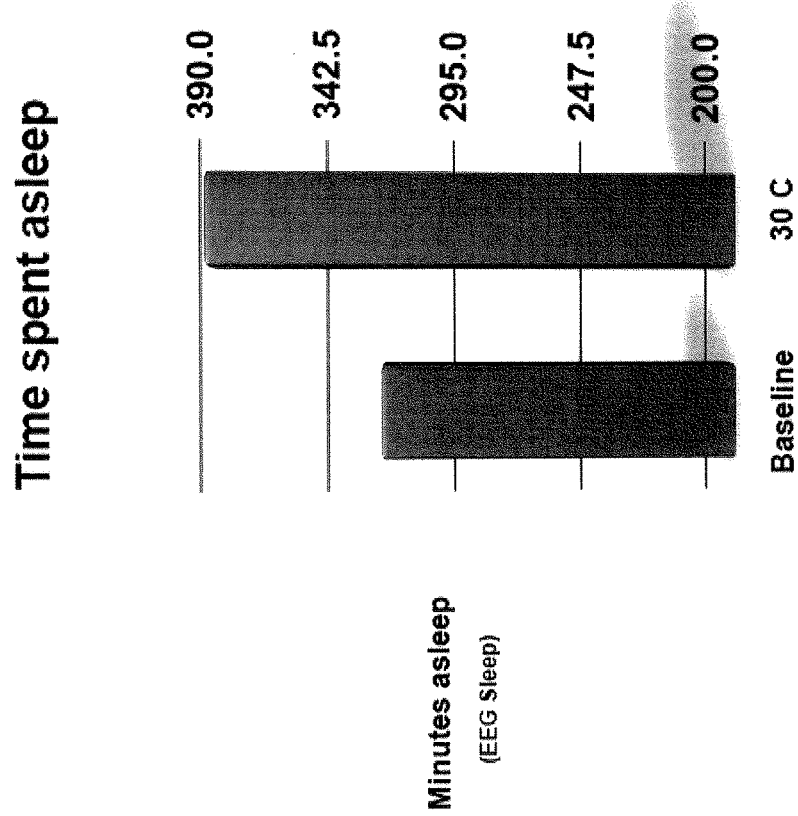

Similarly, subject sleep efficiency was increased dramatically and significantly, as shown in FIG. 5. Sleep efficiency is determined by the time asleep divided by the time in bed, and is a percentage. Time asleep was also determined by ECG evaluation. Compared to baseline, subjects experienced an increase in sleep efficiency from about 67% to greater than 80%. Overall time asleep (over an eight-hour normalized period) from about 322 minutes to about 385 minutes, as shown in FIG. 5 for the same subject population. Note that as used herein "patient" and "subject" may be used interchangeable unless the context indicated otherwise. Any appropriate subject may be indicated including human subjects.

Figure 7:
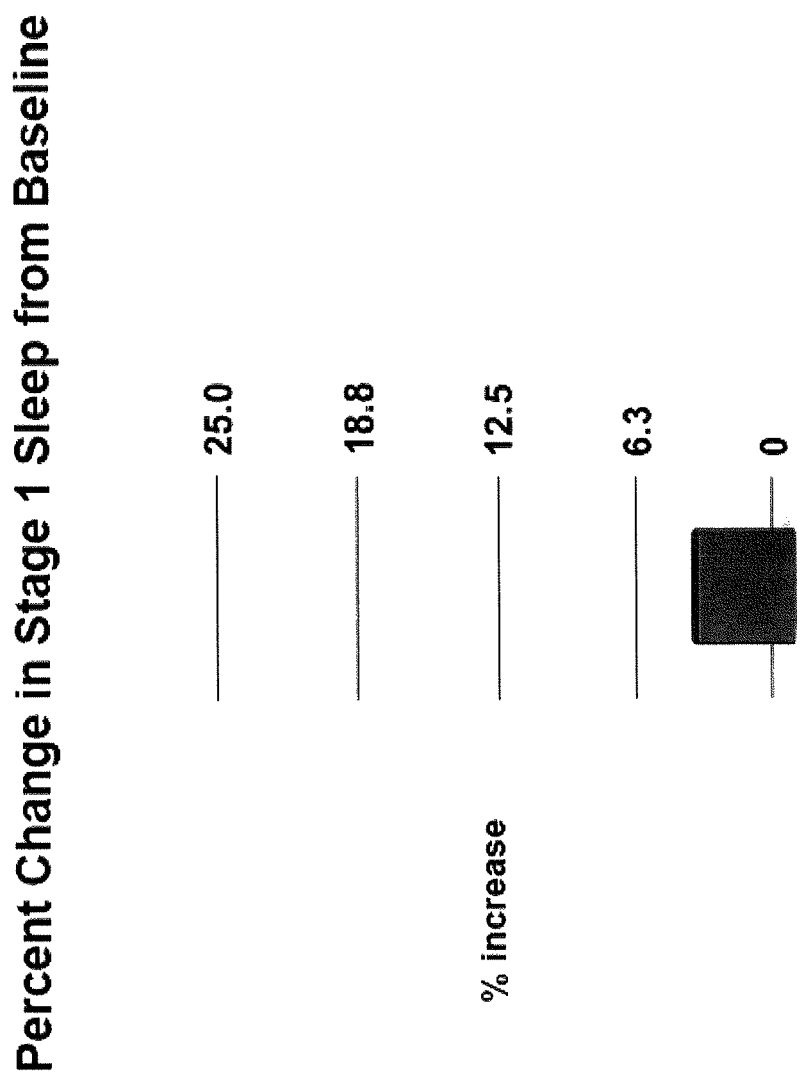

In addition, the quality of sleep, as seen by the sleep stage dynamics, or the amount of time subjects, on average, spent in each of the stages of sleep (stage 1, stage 2, stage 3, REM), improved over baseline. For example, FIG. 7 shows the percent change in stage 1 sleep from baseline between ambient temperature (e.g., baseline) and applying to the forehead a thermal regulator at about 30° C. Each individual patient's percent increase was determined, and FIG. 7 shows the average across the 100 patients receiving 30° forehead temperature regulation over the course of the night. The change in Stage 1 sleep shows an overall increase (approximately 4%) in stage 1 sleep for each patient compared to the same patient's baseline.

Figure 8:
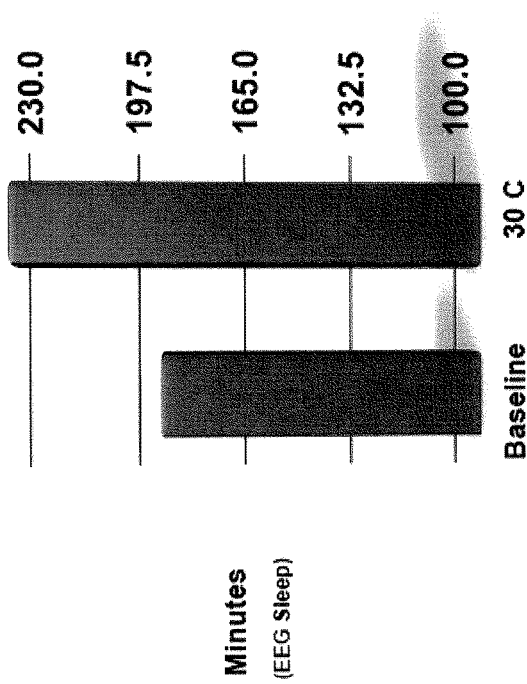
Figure 9:
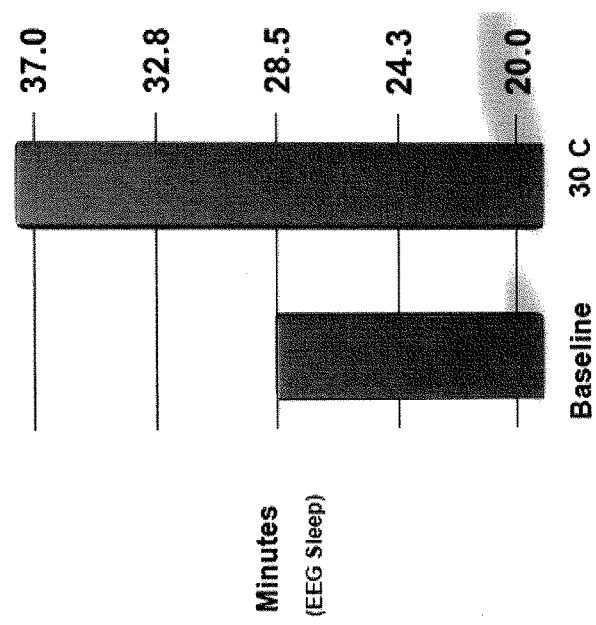
Figure 10:
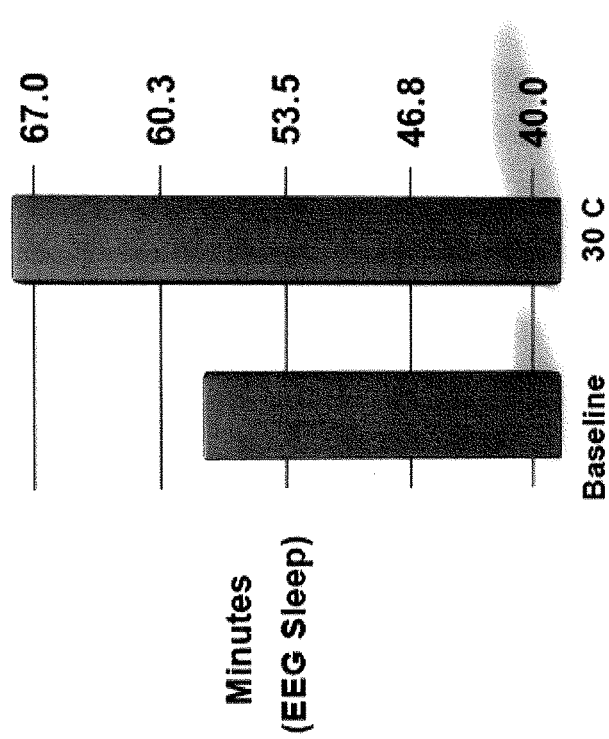
Figure 11:
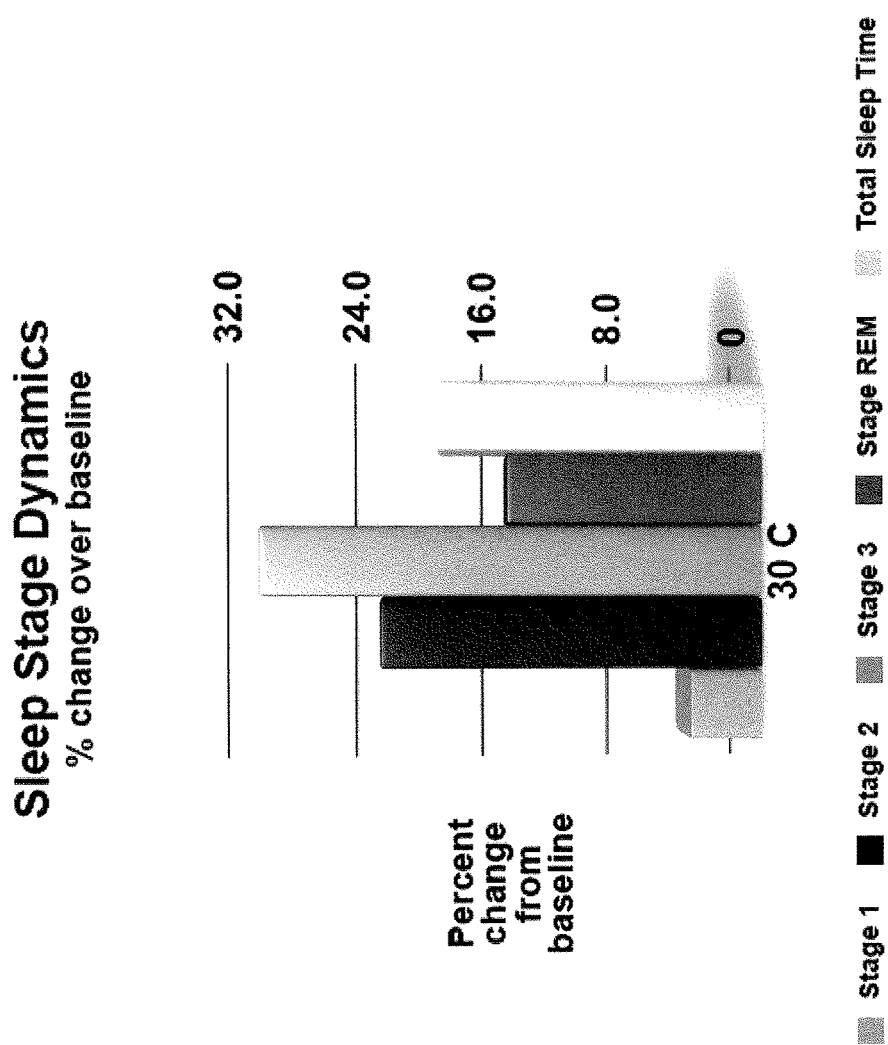

A more dramatic increase in stage 2 sleep ("deeper" sleep than stage 1) was seen, as shown in FIG. 8. Compared to baseline, the same subject's showed a significant increase in stage 2 sleep over an 8-hour sleep period. FIG. 9 shows that stage 3 delta sleep was also significantly increased when subject's foreheads were held to 30° C. during the sleep period. Finally, FIG. 10 shows a substantial effect on REM sleep in the same patients when the applicator was held to 30° C. This data is summarized in FIG. 11, showing the change in sleep stage dynamics as a percent change in baseline averaged across each patient's individual percent change. The change in total sleep time (showing an increase of about 18%) is also shown. The increase in the treated (30° C. at forehead) versus untreated (ambient temp) conditions in the same patients shows a profound effect in increasing both overall sleep and in particular an increase in the deeper sleep stages. These changes are equivalent or greater than changes seen when using pharmacologic sleep aids such as Ambien (Zolpidem).

Figure 12:
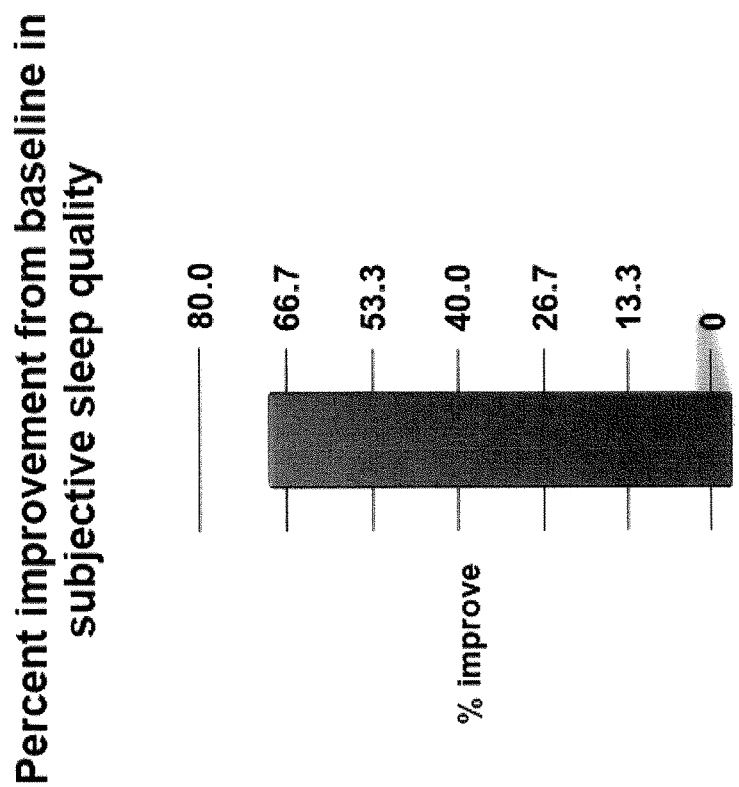
Figure 13A:
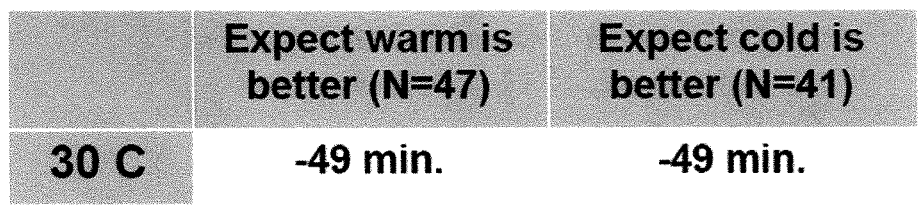
Figure 13B:
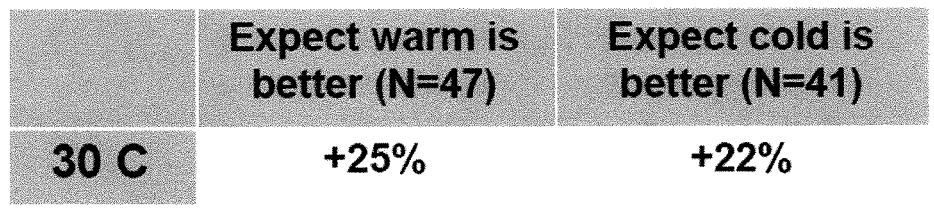

The improvements in sleep were also seen in relative measures such as patient-reported outcomes. For example, as shown in FIG. 12, patient reported sleep quality (subjective sleep quality) was dramatically improved, greater than 67% across the treated patients. This subjective improvement was also highly significant and equivalent to treatment by pharmacological agents. Interestingly, this went against patient expectations as determined by interview results from before the experiment, and shown in FIGS. 13A and 13B. As shown in those results, an equivalent improvement in sleep latency was seen in both subjects who expected to see an improvement by treating with warming (n=47) and those who expected to see an improvement by the opposite, by cooling (n=41); both showed a decrease in sleep latency (time to fall asleep) of about 49 minutes. Similarly, sleep efficiency was also improved about the same amount (e.g., 25% versus 22%) in the same subject groups.

In the study discussed above, it was surprising that regulating the temperature of just the forehead to a temperature that is higher than ambient temperature would have such a profound effect on subject's sleep. Although these experiments were studied on patients with insomnia, the effects are not limited to insomniacs. Similar results should be produced in normal patients as well, or subjects that occasionally experience trouble falling asleep or sustaining sleep. Specifically, the application of thermal control to regulate the temperature of the subject's forehead to a temperature that is warmer than ambient temperature (and/or to a temperature between 25 and 40° C.) may shorten the sleep latency (time to fall asleep), may diminish wakefulness after sleep onset, may increase total sleep time, may shift EEG sleep stages to deeper stages of sleep, may increase stage 3 delta, slow wave sleep, and may improve subjective sleep quality. These effects are independent of treatment expectations regarding effects of the device.

Thus, in some variations, the regional application of the thermal transfer pad (applicator) may be used to enhance sleep. The treatment region may be limited to the forehead, as mentioned above. For example, in one variation, the thermal transfer pad is shaped to cover the region of the forehead that overlies glabrous (non-hairy) skin. The frontal cortex is thought to be uniquely important among body regions for providing thermoregulatory information to the hypothalamus given that it has the highest thermal sensitivity of body surfaces, it has a neural and vascular supply that are specialized for this function and the forehead allows a convenient surface for placing a pad during sleep applications as to minimally interfere with sleep. Thus, an arrangement of the applicator that established thermal transfer between the applicator and the forehead may benefit sleep.

Although the discussion above attempts to provide some theoretical basis for the robust effect seen when the temperature of the forehead is warmed relative to ambient temperature, the invention should not be limited to these theoretical justification for this observed effect, as the method and apparatus may operate effectively regardless of the correctness of the theory of operation. Further, numerous other electrical or mechanical methods for altering forehead skin temperature independent of thermal transfer via warmed circulating fluids are included herein. These methods could be utilized in the regions and manners provided for the purpose of improving sleep by the same underlying brain mechanisms as described, simply utilizing a different method of providing warming in these regions.

In general, these methods may be used to facilitate sleep. For example, the device may be used on the scalp in the region over the area of the forehead to provide a thermoregulatory signal to warm sensitive hypnogenic neurons of the hypothalamus thereby facilitating sleep. The device may be used prior to sleep to aid in sleep onset. Application of the device within sleep has been shown to increase slow wave sleep, increase sleep maintenance, reduce awakenings and increase the time spent asleep across the night. The device may be configured to communicate with the subject's head surface area over the region of the frontal cortex.

The device may be used to improve sleep in at least, but not limited to, the following conditions: improving healthy sleep, improving sleep in insomnia patients; improving sleep in individuals who experience sleeplessness; improving sleep in individuals with neuropsychiatric disorders such as, but not limited to, depression, mood disorders, anxiety disorders, substance abuse, post-traumatic stress disorder, psychotic disorders, manic-depressive illness and personality disorders and any neuropsychiatric patient who experiences sleeplessness; improving sleep in patients with pain, including chronic pain, and headaches, including migraine headaches; improving sleep in patients with sleeplessness or insomnia secondary to other medical disorders such as cardiac, endocrinological, and pulmonary disorders; improving sleep in patients with neurologic disorders where sleeplessness or insomnia occurs including but not limited to tinnitus.

Also described herein are methods for enhancing sleep, and means for implementing these methods, which may include software, hardware and/or firmware, including executable code. For example, also described herein are methods for controlling the temperature of the apparatus. The research study above supports the effects of various rates and timelines for applying or controlling temperatures on the forehead to modulate sleep. The examples and discussion above showed that a fixed temperature of 30° C. improved sleep in insomnia patients. Based on this and additional data, a range of about 25° C. to 40° C. may have similar effects on improving sleep in insomnia patients (or 25° C. to 42° C., or 27° C. to 40° C., or 30° C. to 40° C., etc.). In some variations, a constant temperature of the device can be maintained without variation across the period of use. In other variations, the temperature may be varied.

In general, the thermal transfer pad could be applied prior to getting into bed (prior to "good night time"). In general good night time may refer to the intended time that a patient will (or would like to) fall asleep; this may be the time that a patient goes to bed, or some time thereafter. Thus, for example, the apparatus could be applied to the subject a few minutes before getting into bed, five (5) minutes before going to bed, ten (10) minutes before going to bed, 30 minutes before going to bed, 45 minutes before going to bed, 1 hour prior to getting in to bed, etc., to facilitate the sleep onset process. The research described above indicates that 30° C. is effective in facilitating sleep onset. Neural transmission may occur within seconds, therefore applying the device closer to getting in to bed may enhance the ability of the device to reduce sleep onset. If effects on only sleep onset were desired, the device could be removed prior to the subject falling asleep. In some variations the subject may wear the device before getting to bed (e.g., between an hour to a few minutes before going to bed) and then remove the device immediately before getting to bed. The subject may also keep the device on during sleep.

The apparatus (including the thermal transfer pad) could be applied when or after a subject got into bed, and worn throughout a night of sleep to facilitate sleep across a night of sleep. The research study discussed above indicates that 30° C. may be effective in facilitating deeper sleep. As mentioned, the apparatus could be applied prior to getting in to bed to facilitate the sleep onset process and left on throughout a night of sleep to facilitate sleep across a night of sleep.

In general, the temperature applied by the apparatus may be constant (e.g., held to a constant temperature that is above the ambient temperature at the time the patient is trying to go to sleep; held to a constant predetermined temperature of between about 25° C. and 40° C., such as 30° C., etc.), or it may be varied. For example, the apparatus may be configured, e.g., by including a processor or other control, to vary the temperature application with defined changes delivered across the period of use. The control may be operated by the user so that the user can determine the temperature and/or time course of activation, or the control may be configured to provide the user with a menu of pre-selected choices for temperature and/or time course that are built into the apparatus. Alternatively, the device may automatically select the temperature and/or time course for application.

For example, the apparatus may be configured to vary the time course of temperature to the probability of NREM and REM sleep stage occurrences. It is known that brain temperature as well as brain blood flow and brain metabolism vary in characteristic ways across a night of sleep and is dependent on the stage of sleep an individual is in, as well as the duration of time from the beginning of sleep. NREM sleep stages include lighter stage 1 sleep, deeper stage 2 sleep and deepest stages slow wave sleep with slow wave sleep predominating in the first half of the night. REM sleep occurs cyclically across a night, every 60-90 minutes with progressively longer and more intense REM periods occurring in the latter parts of the night. Brain temperature, blood flow and metabolism tend to lessen in deeper NREM sleep and increases in REM sleep. The degree to which these changes occur are thought to be functionally important for sleep. As discussed above, the apparatus described herein to apply a temperature greater than ambient to a subject's forehead may facilitate the deepening of NREM sleep, by activating warm sensitive neurons in the hypothalamus which subsequently lead to increased slow wave sleep. A variable thermal transfer time course may apply more warming (e.g., a higher temperature differential compared to ambient temperature or absolute temperature, and/or longer time of warming) to the subject's forehead earlier in the night when slow wave sleep tends to be maximal, with less warming (smaller increases over ambient temperature or absolute temperature, and/or shorter periods of warming)

towards the end of the night when REM sleep and natural brain warming would be occurring.

Some disorders, such as depression, have characteristic alterations in REM sleep. The study discussed above demonstrates that altering the temperature of the thermal transfer applicator has predictable effects on the occurrence of REM sleep. One method of treatment may include a variable thermal transfer across the night that is intended to target the occurrence of REM sleep in a therapeutic manner. In depression, for example, where REM sleep duration and intensity seem to be more highly concentrated in the first third of the night, use of 30° C. by the applicator over this period would be expected to inhibit abnormal REM sleep production whereas the use of more neutral temperatures (e.g., ambient) in the latter half of the night may lead to more normal REM sleep production in that part of the night.

Alterations in REM and NREM sleep can occur in a variety of neuropsychiatric disorders. The general principle of altering the temperature of the thermal transfer region of the applicator (which may be referred to herein as a "mask") to facilitate or diminish discrete aspects of deep NREM sleep or REM sleep that are directly related to the specific disorder would be expected to have therapeutic utility specific to the disorder.

In any of the variations described herein, the apparatus may include one or more temperature sensors to detect ambient temperature and/or skin temperature. For example, the apparatus may detect ambient temperature at or near the applicator and/or may detect skin temperature of a subject wearing the applicator. Sensed temperature information may be feed back into the apparatus controller, and may be used, for example, to set or adjust the temperature applied.

The apparatuses described herein may also include or to operate with one or more sensors (or sensing subsystems) configured to determine a subject's sleep state. Sensors or sensing subsystems may include EEG (electroencephalogram) sensors, motion sensors (detecting sleep motions to determine sleep state), and/or body temperature sensors, or other means for determining sleep as known to those of skill in the art; additional examples are provided below.

Altering the temperature properties of the applicator have been shown to have predictable effects on sleep physiology. It would be possible, therefore, to measure the changes in sleep physiology and incorporate them into a feedback loop that then results in changes in the temperature. In this manner, the apparatus controller may therefore adjust the apparatus temperature applied in real time to achieve some desired physiological effect.

In some variations, a variable temperature with defined changes can be delivered across the period of use with the changes linked to feedback from changes in the physiology of the body across a period of use.

For example, the following physiological measures may be monitored and temperature adjusted in real time according to the level of the physiological measure: presence or absence of REM or NREM sleep as assessed by any method of REM/NREM sleep assessment by someone skilled in the art, such as EEG frequency, Heart Rate Variability, Muscle Tone or other means; depth of slow wave sleep, as measured by EEG wave analysis or other means; degree of autonomic arousal as measured by HR variability or other means; galvanic skin response; skin temperature, either at the skin on the head underneath the device, or on skin at some other portion of the head not underneath the device, or peripheral skin temperature, or core body temperature (measured internally or by some external means) or some combined measure assessing thermoregulation of the head and periphery, or core body to peripheral temperature measure.

As mentioned, the person wearing the device may, in some variations, modify the temperature profile across the period of use, with or without the changes linked to feedback. For example, a control on the apparatus may allow the subject wearing the apparatus to adjust the temperature according to their immediate comfort and treatment needs, either up or down some small increments.

In some variations of the apparatus (devices and systems) described herein, an individual can set their go to bed times and desired get out of bed times (and/or good night time), and a preprogrammed algorithm may input start and stop at those times and provide incremental adjustments to occur on a relative basis over this time period. These automated time calculations could be implemented for any variable schedule of thermal transfer rates across any defined period of time.

The applicator may generally include skin-contacting (forehead contacting) thermal transfer region. This thermal transfer region may be configured of any appropriate material. For example, in some variations, the lining of the transfer pad that comes in contact with the skin is a hydrogel allowing for increased surface area contact and increased thermal transfer characteristics. Other materials with appropriate temperature transfer characteristics could be used.

In some variations the applicator includes a lining is combined with dermatologic products that can be rejuvenating for the skin when in contact over the course of a night. For example, creams configured to hydrate the skin and/or apply a medicament to the skin may be used.

In some variations an inner lining can be refreshed on a nightly or less frequent basis that can benefit the skin when applied over the night of sleep. Thus, an applicator, and particularly the skin-contacting portion of the applicator may be configured to be disposable and/or replaceable either daily (e.g., nightly), every other day, every week, etc.

Any of the variations of the apparatuses described herein may also be configured to record, store and/or transmit data about the operation of the device and/or the subject using the device. In the clinical management of a patient, a healthcare provider may want to know certain parameters of the patient and/or device over multiple nights of use such that care can be optimized. In some variations, a memory (e.g. memory card, memory chip, etc.), automatically records all or some parameters and stores them for later display and/or transmission to a healthcare provider. Further, in monitoring their own care, a device user may want to know certain parameters of the patient and/or device over multiple nights of use such that care can be optimized. The apparatus may be configured to display and/or transmit this information, e.g., for uploading to a computing device (computer, mobile communications device, website, etc.).

In some variations, this information could be transferred to a healthcare provider's office or some other central database via the phone or internet or some wireless technology where someone could review the information and provide recommended adjustments in the treatment accordingly.

Examples of information that may be stored could include, but would not be limited to: temperature of the applicator; skin temperature; core body temperature; measures of autonomic variability, depth of sleep as assessed by NREM sleep, EEG power in discrete frequency bands; REM sleep or other sleep staging, etc.; periods of activity and/or wakefulness across the night; subjective measures of sleep depth/comfort/satisfaction; and sleep duration.

Any of the apparatuses (devices and systems) described herein may be configured to operate (or include as part of their operation) a gradual increase/decrease of the temperature (e.g., 'ramping') over a predetermined amount of time. In any of the variations described herein, the temperature may be 'ramped' from ambient to the target temperature, or target temperature range. In general, when a target temperature is described here, it is understood to be a target temperature range, e.g., +/−a range of temperatures centered on the target temperature, where the range may be a between about 0.5 degrees (e.g., +/−0.5° C.), 1 degree (+/−1° C.), 2 degree (+/−2° C.), 3 degree (+/−3° C.), 4 degree (+/−4° C.), 5 degree (+/−5° C.), etc. In some variations the target temperature range may be specified (e.g., between about 26° C. and 40° C. (inclusive), between about 27° C. and 40° C., between about 28° C. and 40° C., between about 29° C. and 40° C., between about 30° C. and 40° C., between about 31° C. and 40° C., between about 32° C. and 40° C., between about 33° C. and 40° C., between about 34° C. and 40° C., between about 35° C. and 40° C., between about 36° C. and 40° C., etc.

For example, in some variations the apparatus may be configured to include an alarm-clock (or 'wakeup') feature in which, at some predetermined/user selected time, the temperature of the applicator is changed (e.g., increased or decreased) to a predetermined temperature (e.g., ambient temperature) to stimulate the subject to wake up. For example, in some variations, the temperature may be set to a range centered on approximately 25° C. (or 30° C., etc.). This temperature may aid the subject in waking up.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of enhancing sleep in a subject, the method comprising:
    securing a thermal transfer region of an applicator in contact with the subject's forehead so that the thermal transfer region does not contact the perioribtal region of the subject's face; and
    maintaining the temperature of the thermal transfer region within a target temperature range that is between 25 and 42° C. to enhance the subject's sleep.

2. The method of claim 1, wherein securing comprises positioning the applicator so that the thermal transfer region does not contact the subject's cheeks.

3. The method of claim 1, further comprising placing a disposable interface on the applicator before securing the applicator, wherein the disposable interface forms at least a part of the thermal transfer region and is configured to contact the subject's forehead.

4. The method of claim 1, wherein securing the applicator comprises positioning the thermal transfer region so that the thermal transfer region does not contact the top or back of the subject's head.

5. The method of claim 1, wherein securing the applicator comprises positioning the thermal transfer region only against the subject's forehead.

6. The method of claim 1, wherein maintaining the temperature of the thermal transfer region comprises maintaining the temperature within the target temperature range that is at least about 0.5° C. greater than an ambient temperature when the ambient temperature is less than about 40° C.

7. The method of claim 1, wherein maintaining the temperature of the thermal transfer region comprises maintaining the temperature within the target temperature range for at least about 15 min.

8. The method of claim 1, wherein maintaining the temperature of the thermal transfer region comprises maintaining the temperature within the target temperature range for at least about 1 hour.

9. The method of claim 1, wherein maintaining the temperature of the thermal transfer region comprises maintaining the temperature within the target temperature range for at least about 4 hours.

10. The method of claim 1, wherein maintaining the temperature of the thermal transfer region comprises maintaining the temperature within a target temperature range for the subject's entire sleep period.

11. The method of claim 1, further comprising varying the target temperature or time course of the temperature within the target temperature range.

12. The method of claim 1, wherein maintaining the temperature comprises warming the thermal transfer region using one or more of: a thermal transfer fluid, a chemical heating element, and a joule heating element.

13. The method of claim 1, wherein the method of enhancing sleep is a method of treating insomnia and wherein securing the thermal transfer region comprises securing the thermal transfer region on a subject having insomnia.

14. A method of enhancing sleep in a subject, the method comprising:
    placing a disposable interface on an applicator, wherein the disposable interface forms at least a part of a thermal transfer region of the applicator and is configured to contact the subject's forehead;
    securing the thermal transfer region of the applicator against the subject's forehead; and
    maintaining the temperature of the thermal transfer region within a target temperature range that is between 25 and 42° C. for at least 15 min, to enhance the subject's sleep.

15. The method of claim 14, wherein securing the thermal transfer region of the applicator comprises placing the thermal transfer region so that the thermal transfer region only contacts the subject's forehead.

16. The method of claim 14, wherein securing the thermal transfer region of the applicator comprises placing the thermal transfer region so that the thermal transfer region does not contact the perioribtal, or cheek regions of the subject's face.

17. The method of claim 14, wherein maintaining the temperature comprises maintaining the temperature of the thermal transfer region within the target temperature range for at least 30 min.

18. The method of claim 14, wherein maintaining the temperature comprises maintaining the temperature of the thermal transfer region within the target temperature range for at least 1 hour.

19. A method of decreasing sleep onset latency, the method comprising:
    securing an applicator on a subject's forehead so that a thermal transfer region of the applicator contacts the subject's forehead, wherein the thermal transfer region does not contact the perioribtal or cheek regions of the subject's face; and
    reducing sleep onset latency by maintaining the temperature of the thermal transfer region within a target temperature within a target temperature range that is between 25 and 42° C. for at least 15 minutes.

20. The method of claim 19, further comprising placing a disposable interface on the applicator before positioning the applicator, wherein the disposable interface forms at least a part of the thermal transfer region and is configured to contact the subject's forehead.

21. The method of claim 19, wherein securing the applicator comprises positioning the thermal transfer region so that the thermal transfer region does not contact the top or back of the subject's head.

22. The method of claim 19, wherein securing the applicator comprises positioning the thermal transfer region only against the subject's forehead.

23. The method of claim 19, wherein maintaining the temperature of the thermal transfer region comprises maintaining the temperature within the target temperature for at least about 1 hour.

24. The method of claim 19, wherein maintaining the temperature of the thermal transfer region comprises maintaining the temperature within the target temperature for at least about 4 hours.

25. The method of claim 19, wherein maintaining the temperature of the thermal transfer region comprises maintaining the temperature within the target temperature for the subject's entire sleep period.

26. A method of increasing sleep duration, the method comprising:

securing an applicator on the forehead of a subject so that a thermal transfer region of the applicator contacts the subject's forehead, wherein the thermal transfer region does not contact the perioribtal or cheek regions of the subject's face; and increasing sleep duration by maintaining the temperature of the thermal transfer region within a target temperature within a target temperature range that is between 25 and 42° C. for at least 15 minutes.

\* \* \* \* \*